(12) United States Patent
Hirakawa

(10) Patent No.: US 8,585,585 B2
(45) Date of Patent: Nov. 19, 2013

(54) ENDOSCOPIC FORM DETECTION DEVICE AND FORM DETECTING METHOD OF INSERTION SECTION OF ENDOSCOPE

(75) Inventor: Katsumi Hirakawa, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 90 days.

(21) Appl. No.: 13/229,345

(22) Filed: Sep. 9, 2011

(65) Prior Publication Data

US 2012/0059221 A1    Mar. 8, 2012

Related U.S. Application Data

(63) Continuation of application No. PCT/JP2011/059636, filed on Apr. 19, 2011.

(30) Foreign Application Priority Data

May 31, 2010   (JP) ................................. 2010-125153

(51) Int. Cl.
*A61B 1/04*   (2006.01)
*A61B 5/05*   (2006.01)
*A61B 1/00*   (2006.01)
*G06K 9/00*   (2006.01)

(52) U.S. Cl.
USPC ............................ 600/117; 600/145; 382/103

(58) Field of Classification Search
USPC ......... 600/117, 145, 420, 431, 433, 424, 101, 600/109; 604/528, 523; 606/14, 77; 348/65
See application file for complete search history.

(56) References Cited

U.S. PATENT DOCUMENTS 5,971,976 A * 10/1999 Wang et al. ....................... 606/1
6,059,718 A * 5/2000 Taniguchi et al. ............ 600/117
6,564,088 B1 * 5/2003 Soller et al. .................... 600/478
6,845,190 B1 * 1/2005 Smithwick et al. ............. 385/25
7,935,048 B2 * 5/2011 Yaron et al. .................... 600/117
8,073,528 B2 * 12/2011 Zhao et al. ..................... 600/424

(Continued)

FOREIGN PATENT DOCUMENTS

| JP | A-11-019027 | 1/1999 |
| JP | A-2000-175862 | 6/2000 |
| JP | A-2007-319622 | 12/2007 |
| JP | A-2009-153863 | 7/2009 |
| JP | A-2010-104426 | 5/2010 |
| WO | WO 2007/013350 A1 | 2/2007 |

OTHER PUBLICATIONS

Jul. 19, 2012 Search Report issued in European Patent Application No. 11789549.0.

(Continued)

*Primary Examiner* — John P Leubecker
*Assistant Examiner* — Ronald D Colque
(74) *Attorney, Agent, or Firm* — Oliff & Berridge, PLC

(57) ABSTRACT

An endoscopic form detection device includes a posture detecting section configured to detect a posture of each of sensor units based on measurement data in the sensor unit, and a linear form detecting section configured to detect a detected linear form of an inserting section on an assumption that a form between the respective sensor units is a linear link whose dimension is equal to an inter-sensor dimension based on the detected posture of each of the sensor units. The endoscopic form detection device includes a form correcting section configured to compensate at least a position of each of the sensor units by using a particle filter, and configured to detect a corrected form obtained by correcting the detected linear form.

16 Claims, 14 Drawing Sheets

(56) References Cited

U.S. PATENT DOCUMENTS

| | | | |
|---|---|---|---|
| 8,108,072 B2* | 1/2012 | Zhao et al. | 700/250 |
| 8,147,503 B2* | 4/2012 | Zhao et al. | 606/130 |
| 2006/0258938 A1* | 11/2006 | Hoffman et al. | 600/424 |
| 2007/0106114 A1* | 5/2007 | Sugimoto et al. | 600/117 |
| 2008/0009674 A1* | 1/2008 | Yaron | 600/117 |
| 2008/0015434 A1* | 1/2008 | Rubinstein et al. | 600/431 |
| 2008/0221592 A1 | 9/2008 | Kawai | |
| 2009/0088634 A1* | 4/2009 | Zhao et al. | 600/427 |
| 2009/0088773 A1* | 4/2009 | Zhao et al. | 606/130 |
| 2009/0088897 A1* | 4/2009 | Zhao et al. | 700/250 |
| 2009/0175518 A1 | 7/2009 | Ikuma et al. | |
| 2010/0099951 A1* | 4/2010 | Laby et al. | 600/144 |
| 2011/0098533 A1* | 4/2011 | Onoda et al. | 600/117 |
| 2011/0184238 A1* | 7/2011 | Higgins et al. | 600/117 |

OTHER PUBLICATIONS

Arulampalam et al., "A Tutorial on Particle Filters for Online Nonlinear/Non-Gaussian Bayesian Tracking," *IEEE Transactions on Signal Processing*, Feb. 1, 2002, pp. 174-188, vol. 50 No. 2, New York, New York, United States.

International Search Report issued in International Application No. PCT/JP2011/059636 dated May 31, 2011 (with translation).

Dec. 28, 2010 International Preliminary Report on Patentability issued in International Application No. PCT/2010/069032.

* cited by examiner

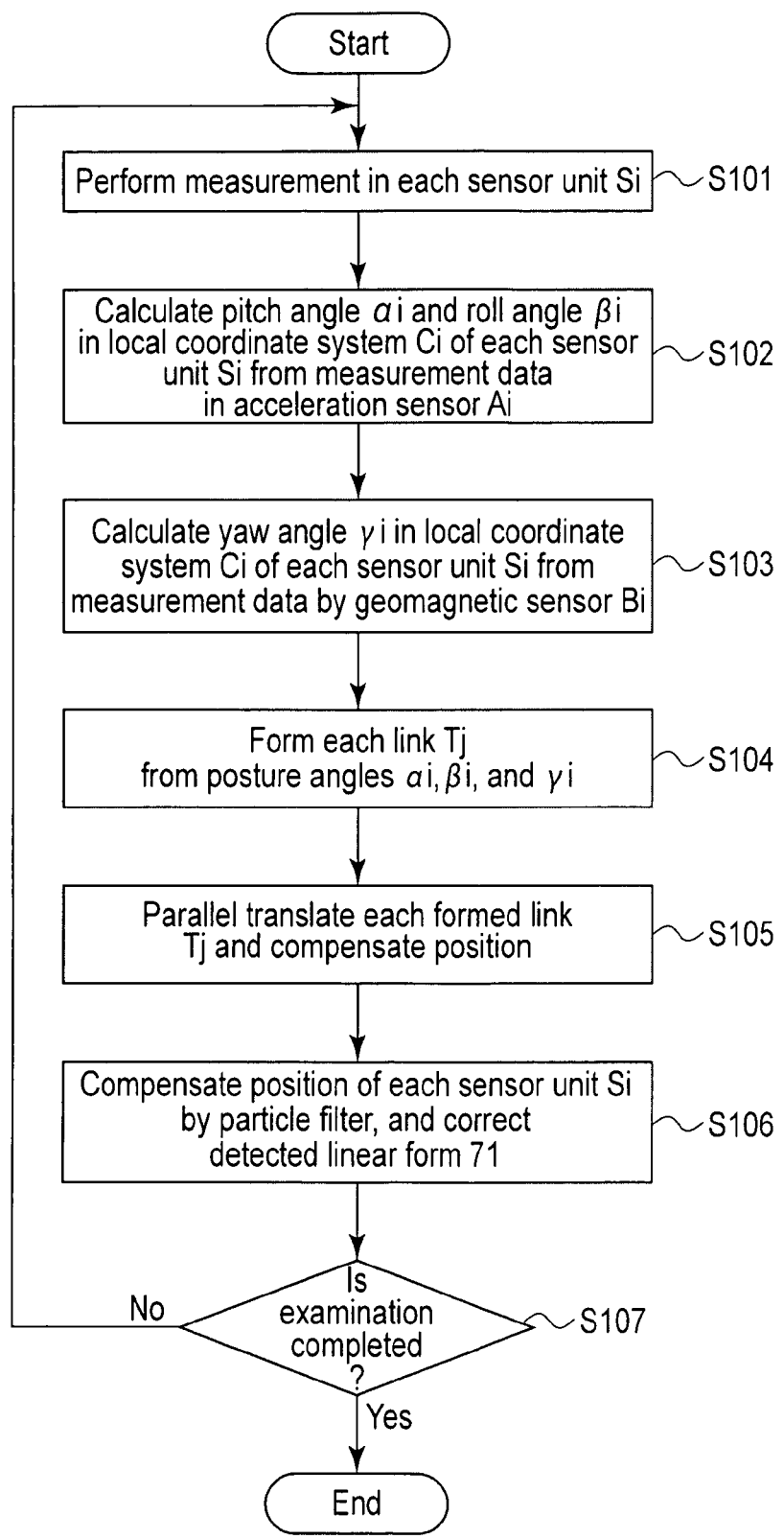
F I G. 4

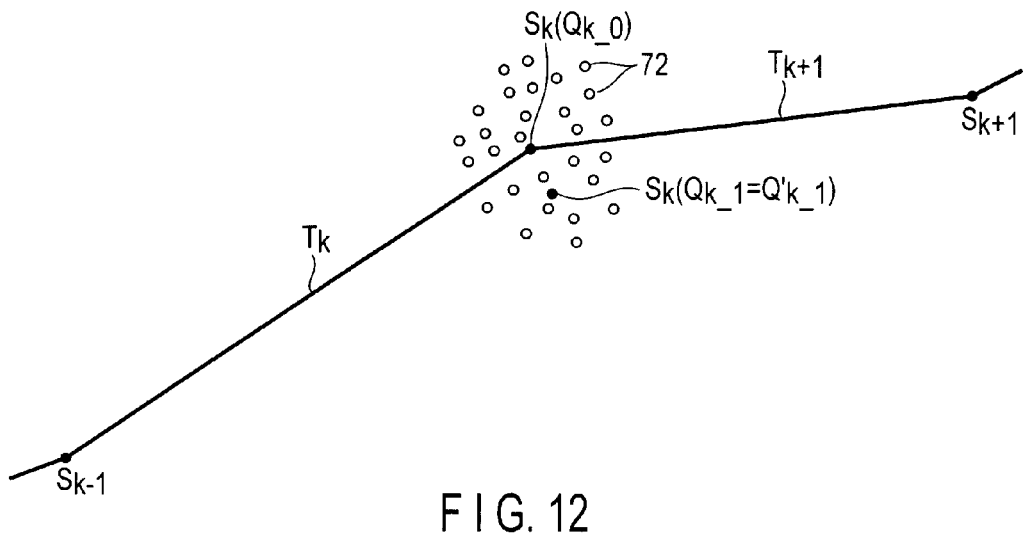
F I G. 12
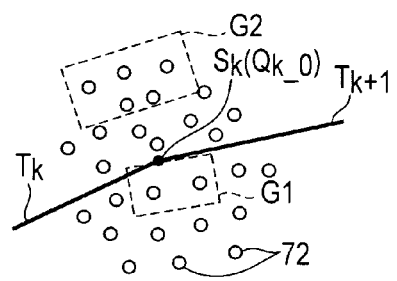
F I G. 13A
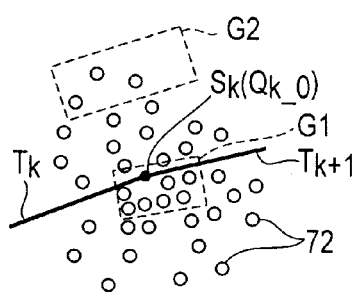
F I G. 13B

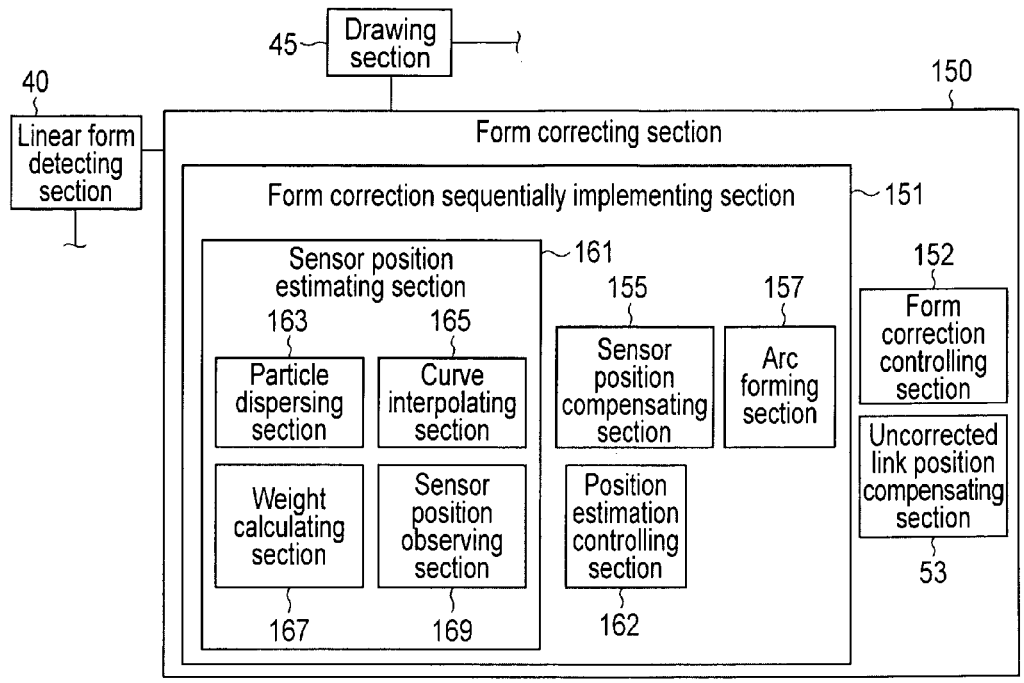
F I G. 16
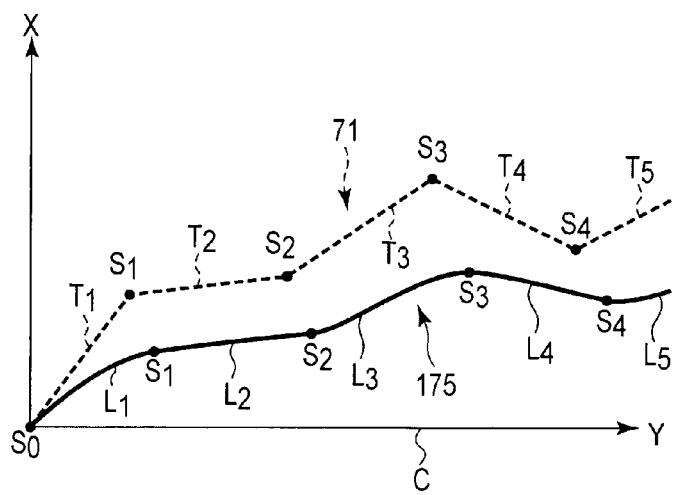
F I G. 17

ENDOSCOPIC FORM DETECTION DEVICE AND FORM DETECTING METHOD OF INSERTION SECTION OF ENDOSCOPE

CROSS REFERENCE TO RELATED APPLICATIONS

This application is a Continuation Application of PCT Application No. PCT/JP2011/059636, filed Apr. 19, 2011 and based upon and claiming the benefit of priority from prior Japanese Patent Application No. 2010-125153, filed May 31, 2010, the entire contents of all of which are incorporated herein by reference.

BACKGROUND OF THE INVENTION

1. Field of the Invention

The present invention relates to an endoscopic form detection device including an endoscope configured to be inserted into a body cavity and a form detecting method of an inserting section of the endoscope.

2. Description of the Related Art

In recent years, an endoscopic form detection device that can detect a form of an inserting section of an endoscope has been put to practical use. Jpn. Pat. Appln. KOKAI Publication No. 2000-175862 discloses an endoscope insertion form detection device including source coils disposed to an inserting section of an endoscope configured to be inserted into a body cavity. In this endoscope insertion form detection device, positions of the respective source coils are detected by a sense coil provided outside a body. Further, based on the detected positions of the source coils, a form of the inserting section of the endoscope is detected.

Furthermore, Jpn. Pat. Appln. KOKAI Publication No. 2007-319622 discloses an endoscope device including two sensors disposed to an inserting section of an endoscope. In this endoscope device, a sensor on a proximal end side is determined as a reference, and a position and a posture of a sensor on a distal end side are detected. The sensor on the proximal end side is arranged near a proximal end of a bending section, and the sensor on the distal end side is arranged at a distal-end hard section. A bending angle and a bending direction of the bending section are calculated by detecting the position and the posture of the sensor on the distal end side with respect to the sensor on the proximal end side.

Further, Jpn. Pat. Appln. KOKAI Publication No. 11-19027 discloses an endoscopic form detection device including gyroscopes disposed to an inserting section of an endoscope. In this endoscopic form detection device, a posture in a predetermined region (a region to which the gyroscope is disposed) of the inserting section of the endoscope is detected by the gyroscope. Furthermore, a form of the inserting section is detected based on the detected posture in the predetermined region.

BRIEF SUMMARY OF THE INVENTION

According to one aspect of the invention, an endoscopic form detection device includes that an endoscope including an inserting section in which sensor units are arranged in longitudinal directions at intervals of a predetermined inter-sensor dimension; a posture detecting section configured to detect a posture of each of the sensor units based on measurement data in the sensor unit; a linear form detecting section configured to detect a detected linear form of the inserting section of the endoscope on an assumption that a form between the respective sensor units is a linear link whose dimension is equal to the inter-sensor dimension based on the posture of each of the sensor units detected by the posture detecting section; and a form correcting section configured to compensate at least a position of each of the sensor units by using a particle filter, and configured to detect a corrected form obtained by correcting the detected linear form detected by the linear form detecting section.

According to one another aspect of the invention, A form detecting method of an inserting section of an endoscope, the method includes that performing measurement by using sensor units arranged in longitudinal directions of the inserting section of the endoscope at intervals of a predetermined inter-sensor dimension; detecting a posture of each sensor unit based on measurement data in each sensor unit by using a posture detecting section; detecting a detected linear form of the inserting section of the endoscope by using a linear form detecting section on an assumption that a form between the respective sensor units is a linear link whose dimension is equal to the inter-sensor dimension based on the posture of each sensor unit detected by the posture detecting section; and compensating at least a position of each sensor unit by using a particle filter, and detecting a corrected form obtained by correcting the detected linear form detected by the linear form detecting section by using a form correcting section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 4 is a flowchart showing a method of detecting a form of the inserting section of the endoscope in a stationary state according to the first embodiment;

FIG. 12 is a schematic view explaining processing in a sensor position estimating section of the sensor position observing section of the form correcting section according to the first embodiment;

FIG. 13A is a schematic view showing a dispersed state of particles dispersed at the time of observation immediately before current observation in the second or subsequent observation in the sensor position observing section of the form correcting section according to the first embodiment;

FIG. 13B is a schematic view showing a dispersed state of particles dispersed at the time of the current observation in the second or subsequent observation in the sensor position observing section of the form correcting section according to the first embodiment;

FIG. 16 is a block diagram showing a configuration of a form correcting section of an endoscopic form detection device according to a second embodiment of the present invention;

FIG. 17 is a schematic view showing a corrected form subjected to form correction by the form correcting section of the endoscopic form detection device according to the second embodiment;

DETAILED DESCRIPTION OF THE INVENTION

First Embodiment

A first embodiment according to the present invention will now be described with reference to FIG. 1 to FIG. 15.

Figure 1:
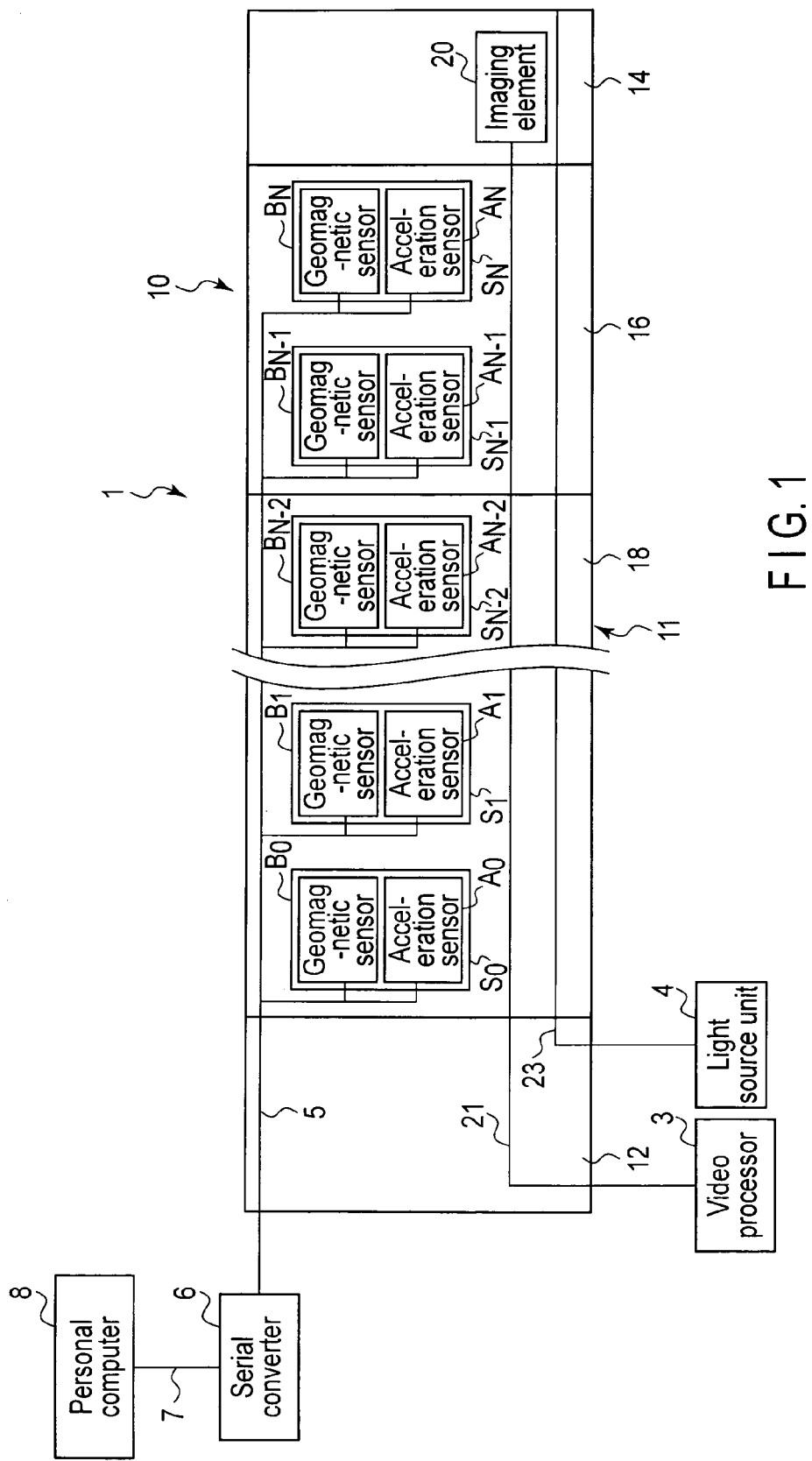
FIG. 1 is a block diagram showing a configuration of an endoscopic form detection device according to a first embodiment of the present invention.

FIG. 1 is a view showing an endoscopic form detection device 1 according to a first embodiment. As shown in FIG. 1, an endoscope 10 of the endoscopic form detection device 1 includes an inserting section 11 configured to be inserted into a body cavity and an operating section 12 provided to a proximal end side of the inserting section 11. The inserting section 11 includes a distal-end hard section 14 provided at a most distal end side; a bending section 16 provided to the proximal end side of the distal-end hard section 14, and an elongated flexible tube section 18 provided to the proximal end side of the bending section 16.

An imaging element 20 such as a CCD configured to image a subject is provided in the distal-end hard section 14. One end of an imaging signal line 21 is connected to the imaging element 20. The imaging signal line 21 is extended to the outside of the endoscope 10 from the operating section 12 through the inserting section 11, and the other end of the imaging signal line 21 is connected to a video processor 3 which is an image processing unit. Furthermore, a light guide 23 configured to guide illumination light applied to a subject is extended to an illumination window (not shown) of the distal-end hard section 14 along longitudinal directions in the inserting section 11. The light guide 23 is extended to the outside of the endoscope 10 from the operating section 12 and connected to a light source unit 4.

Moreover, one end of each of four bending operation wires (not shown) as bending operation transmission members is connected to a distal end portion of the bending section 16 in the inserting section 11. The other end of each bending operation wire is connected to a bending operation knob (not shown), which is a bending operating section provided to the operating section 12, through the flexible tube section 18. The bending operation wires move in the longitudinal directions by operations using the bending operation knob. The bending section 16 is configured to bend in up-down directions and left-right directions of the endoscope 10 by the movement of the bending operation wires.

A plurality of (N+1 in this embodiment) sensor units $S_0$ to $S_N$ are provided in the inserting section 2. The respective sensor units $S_i$ (i=0, 1, 2, . . . , N) are arranged to be apart from each other in the longitudinal directions at fixed intervals (=50 mm). That is, respective sensor units $S_i$ are arranged to be apart from each other in the longitudinal directions at intervals of a predetermined inter-sensor dimension l. Here, for example, the sensor unit $S_0$ provided on a most proximal end side is arranged in a proximal end portion of the flexible tube section 18, and the sensor unit $S_N$ provided on the most distal end side is arranged in the distal end portion of the bending section 16. Each sensor unit $S_i$ includes an accelerator sensor $A_i$ configured to measure acceleration, and a geomagnetic sensor $B_i$ configured to measure earth magnetism.

Figure 2:
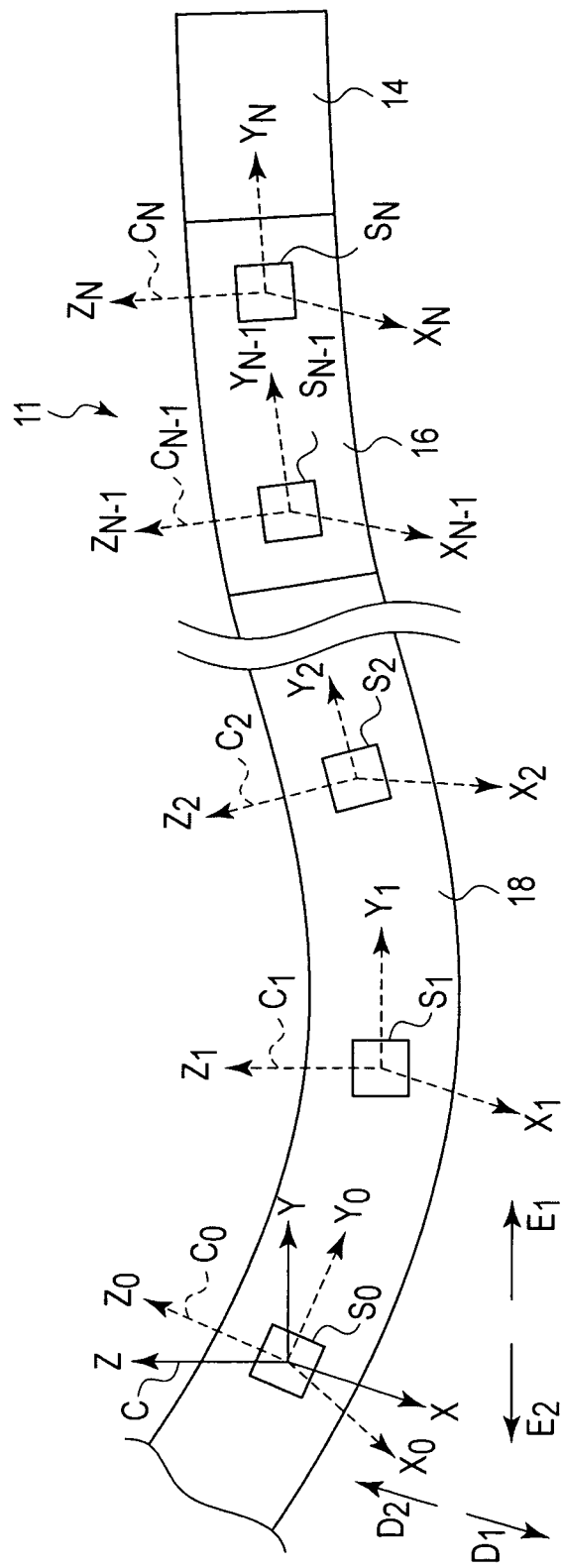
FIG. 2 is a schematic view showing a configuration of an inserting section of an endoscope according to the first embodiment.

FIG. 2 is a view showing the inserting section 11 of the endoscope 10. As shown in FIG. 2, each sensor unit $S_i$ has a local coordinate system $C_i$ (indicated by a dotted line in FIG. 2) having an origin at the center of the sensor unit $S_i$, and also having an $X_i$ axis, a $Y_i$ axis, and a $Z_i$ axis. Here, the $X_i$ axis directions coincide with the left-right directions of the endoscope 10 at the center of the sensor unit $S_i$, and a right direction of the endoscope 10 as seen from the proximal end side is determined to be positive. The $Y_i$ axis directions coincide with the longitudinal directions at the center of the sensor unit $S_i$, and the distal end side direction is determined to be positive. The $Z_i$ axis directions coincide with the up-down directions of the endoscope 10 at the center of the sensor unit $S_i$, and an up direction of the endoscope 10 is determined to be positive. The acceleration sensor $A_i$ is configured to measure an $X_i$ axis directions component, a $Y_i$ axis directions component, and a $Z_i$ axis directions component of acceleration at the origin of the local coordinate system $C_i$.

Furthermore, in the endoscopic form detection device 1, a global coordinate system C (indicated by a solid line in FIG.

2) having an X axis, a Y axis, and a Z axis is defined with the center of the sensor unit $S_0$ provided on the most proximal end side being determined as an origin. Here, the global coordinate system C is a rectangular Cartesian coordinate system for a right-hand system with the center of the sensor unit $S_0$ provided on the most proximal end side determined as an origin. The X-axis directions coincide with predetermined directions (directions parallel to arrows D1 and D2 in FIG. 2 in this embodiment) perpendicular to vertical directions in which gravity functions, and a direction of the arrow D1 in FIG. 2 is determined to be positive. The Y axis directions coincide with directions (directions parallel to arrows E1 and E2 in FIG. 2 in this embodiment) perpendicular to the vertical directions and the X axis directions, and a direction of the arrow E1 in FIG. 2 is determined to be positive. The Z axis directions coincide with the vertical directions, and an up direction (direction extending from a back side to a front side of a paper sheet) of the vertical directions is determined to be positive. It is to be noted that a positive direction of the X axis directions of the global coordinate system is determined as a magnetic north direction for convenience of explanation.

Each local coordinate system $C_i$ is a coordinate system obtained by rotating the global coordinate system C $\alpha_i$ about the X axis, $\beta_i$ about the Y axis, and $\gamma_i$ about the Z axis and parallel translating the origin from the center of the sensor unit $S_0$ provided on the most proximal end side to the center of the sensor unit $S_i$. Here, $\alpha_i$ is referred to as a pitch angle, $\beta_i$ is referred to as a roll angle, $\gamma_i$ is referred to as a yaw angle, and three angles, i.e., the pitch angle $\alpha_i$, the roll angle $\beta_i$, and the yaw angle $\gamma_i$ will be generically referred to as posture angles. A clockwise direction of each posture angle $\alpha_i$, $\beta_i$, or $\gamma_i$ seen from a negative direction of each of the X axis, the Y axis, and the Z axis is determined to be positive. A posture of the sensor unit $S_i$ can be detected by calculating values of the posture angles $\alpha_i$, $\beta_i$, and $\gamma_i$.

As shown in FIG. 1, a serial bus 5 such as I2C is connected to the acceleration sensor $A_i$ and the geomagnetic sensor $B_i$ of each sensor unit $S_i$. The serial bus 5 is extended to the outside of the endoscope 10 from the operating section 12 through the inside of the inserting section 11, and its proximal end is connected to a serial converter 6. The serial converter 6 is configured to convert a serial signal of measurement data input from each sensor unit $S_i$ through the serial bus 5 into a USB signal. One end of a USB cable 7 is connected to the serial converter 6. The other end of the USB cable 7 is connected to a personal computer 8. The USB signal of the measurement data in each sensor unit $S_i$ is configured to be input to the personal computer 8 from the serial converter 6.

Figure 3:
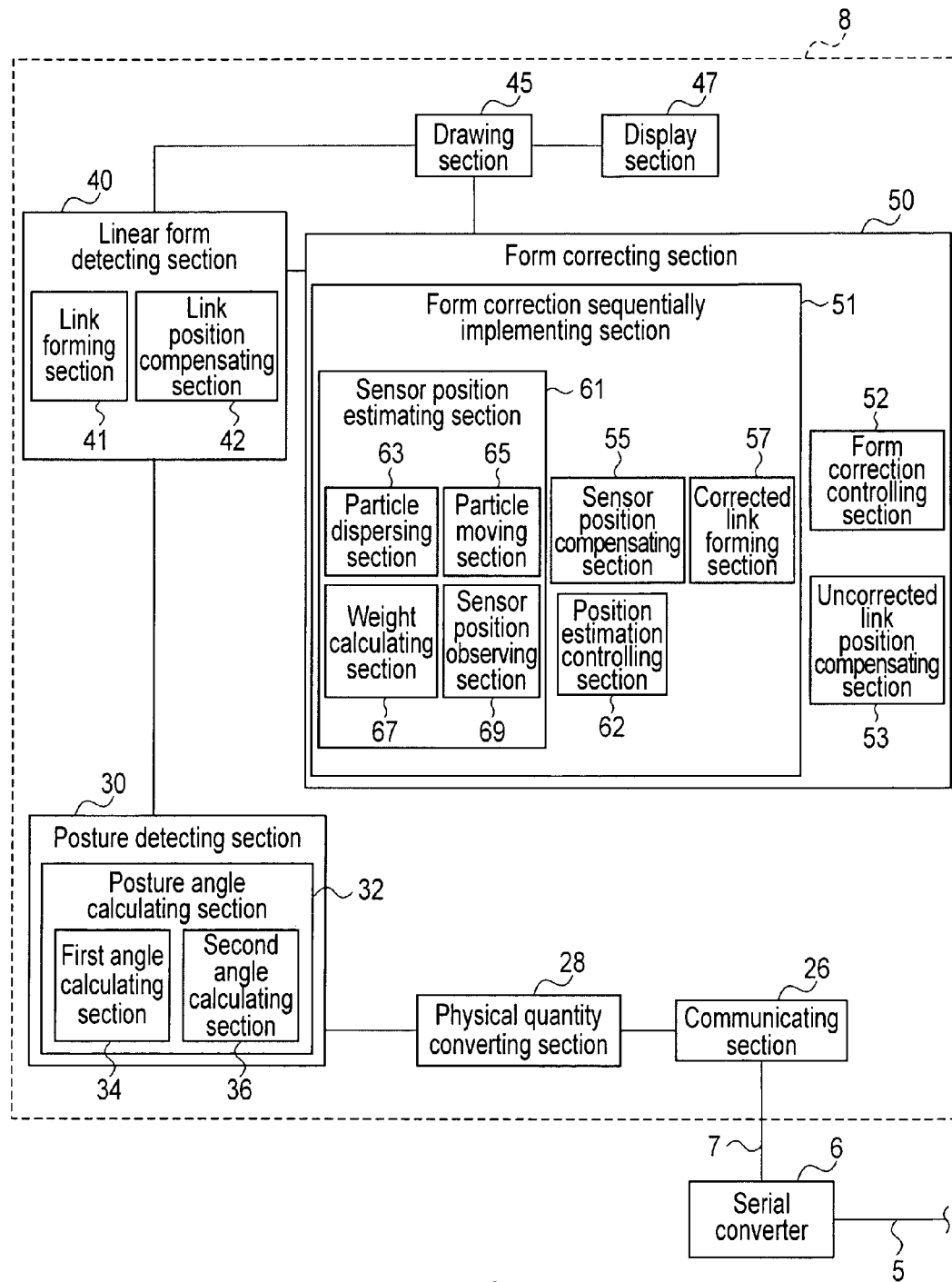
FIG. 3 is a block diagram showing a configuration of a personal computer of the endoscopic form detection device according to the first embodiment.

FIG. 3 is a view showing a configuration of the personal computer 8. As shown in FIG. 3, the personal computer 8 includes a communicating section 26 connected to the serial converter 6 through the USB cable 7. The communicating section 26 is configured to receive the measurement data in each sensor unit $S_i$. A physical quantity converting section 28 is connected to the communicating section 26. The physical quantity converting section 28 is configured to convert the measurement data in each sensor unit $S_i$ received by a communicating section 26 into a physical quantity by using an offset, a gain, and others.

A posture detecting section 30 is connected to the physical quantity converting section 28. The posture detecting section 30 is configured to detect a posture of each sensor unit $S_i$ based on the measurement data in each sensor unit $S_i$. The posture detecting section 30 includes a posture angle calculating section 32 configured to calculate the three posture angles $\alpha_i$, $\beta_i$, and $\gamma_i$ as rotational angles in the local coordinate system $C_i$ of each sensor unit $S_i$ about the X axis, the Y axis, and the Z axis from the global coordinate system C based on measurement data obtained by the acceleration sensor $A_i$ and the geomagnetic sensor $B_i$ of each sensor unit $S_i$. The posture angle calculating section 32 includes a first angle calculating section 34 configured to calculate a pitch angle $\alpha_i$ as a rotational angle in the local coordinate system $C_i$ of each sensor unit $S_i$ about the X axis from the global coordinate system C and a roll angle $\beta_i$ as a rotational angle in the local coordinate system $C_i$ of each sensor unit $S_i$ about the Y axis from the global coordinate system C based on measurement data in the acceleration sensor $A_i$ and the geomagnetic sensor $B_i$ of each sensor unit $S_i$. Moreover, the posture angle calculating section 32 also includes a second angle calculating section 36 configured to calculate a yaw angle $\gamma_i$ as a rotational angle in the local coordinate system $C_i$ of each sensor unit $S_i$ about the Z axis from the global coordinate system C based on the geomagnetic data in the geomagnetic sensor $B_i$ of each sensor unit $S_i$.

A method of detecting a posture of each sensor unit $S_i$ by the posture detecting section 30 will now be described. FIG. 4 is a flowchart showing a form detecting method of the inserting section 11 in a stationary state in which the inserting section 11 of the endoscope 10 is stopped. As shown in FIG. 4, when detecting a form of the inserting section 11, each sensor unit $S_i$ first performs measurement (a step S101), and the posture detecting section 30 acquires measurement data in each sensor unit $S_i$. Additionally, the posture angle calculating section 32 calculates the three posture angles $\alpha_i$, $\beta_i$, and $\gamma_i$ in the local coordinate system $C_i$ of each sensor unit $S_i$.

When calculating the posture angles $\alpha_i$, $\beta_i$, and $\gamma_i$, the first angle calculating section 34 first calculates the pitch angle $\alpha_i$ and the roll angle $\beta_i$ in the local coordinate system $C_i$ of each sensor unit $S_i$ (a step S102) based on the measurement data in the acceleration sensor $A_i$ of each sensor unit $S_i$. Here, the posture angles $\alpha_i$, $\beta_i$, and $\gamma_i$ are determined as a (Z, X, Y) type that rotates in the order of the yaw angle $\gamma_i$, the pitch angle $\alpha_i$, and the roll angle $\beta_i$. Therefore, a rotation matrix from the global coordinate system C to the local coordinate system $C_i$ is as follows:

$$C_{Bi}^{G} = R_{Zi} R_{Xi} R_{Yi} \tag{1}$$

$$= \begin{bmatrix} \cos\gamma_i & -\sin\gamma_i & 0 \\ \sin\gamma_i & \cos\gamma_i & 0 \\ 0 & 0 & 1 \end{bmatrix} \begin{bmatrix} 1 & 0 & 0 \\ 0 & \cos\alpha_i & -\sin\alpha_i \\ 0 & \sin\alpha_i & \cos\alpha_i \end{bmatrix} \begin{bmatrix} \cos\beta_i & 0 & \sin\beta_i \\ 0 & 1 & 0 \\ -\sin\beta_i & 0 & \cos\beta_i \end{bmatrix}$$

$$= \begin{bmatrix} -\sin\gamma_i \cdot \sin\alpha_i \cdot \sin\beta_i + \cos\beta_i \cdot \cos\gamma_i & -\sin\gamma_i \cdot \cos\alpha_i & \sin\gamma_i \cdot \sin\alpha_i \cdot \cos\beta_i + \sin\beta_i \cdot \cos\gamma_i \\ \cos\gamma_i \cdot \sin\alpha_1 \sin\beta_1 + \cos\beta_i \cdot \sin\gamma_i & \cos\gamma_i \cdot \cos\alpha_i & -\cos\gamma_i \cdot \sin\alpha_i \cdot \cos\beta_i + \sin\beta_i \cdot \sin\gamma_i \\ -\cos\alpha_i \cdot \sin\beta_1 & \sin\alpha_i & \cos\alpha_i \cdot \cos\beta_i \end{bmatrix}$$

In the stationary state in which the inserting section 11 is stopped, gravitational acceleration alone functions downward in the vertical directions. That is, in both the global coordinate system C and the local coordinate system $C_i$, the gravitational acceleration alone functions downward in the vertical directions. Therefore, at this time, an X axis directions component, a Y axis directions component, and a Z axis directions component of an acceleration vector in the global coordinate system C are as follows:

$$\dot{a}_{th}=[0\ 0\ -g]^T \quad (2)$$

Further, it is assumed that an $X_i$ axis directions component, a $Y_i$ axis directions component, and a $Z_i$ axis directions component of an acceleration vector in the local coordinate system $C_i$ measured by the acceleration sensor Ai are as follows:

$$\dot{a}_{obsi}=[a_{Bi\_X}\, a_{Bi\_Y}\, a_{Bi\_Z}]^T \quad (3)$$

Here, the local coordinate system $C_i$ is a coordinate system obtained by rotating the global coordinate system C in the order of the yaw angle $\gamma_i$, the pitch angle $\alpha_i$, and the roll angle $\beta_i$. Therefore, based on Expression (1) to Expression (3), acceleration components observed in the local coordinate system $C_i$ are as follows:

$$\dot{a}_{obsi} = (C_{Bi}^G)^T \dot{a}_{th} = -g \begin{bmatrix} -\cos\alpha_i \cdot \sin\beta_i \\ \sin\alpha_i \\ \cos\alpha_i \cdot \cos\beta_i \end{bmatrix} \begin{matrix} (4.1) \\ (4.2) \\ (4.3) \end{matrix}$$

Here, when a square of Expression (4.1) is added to a square of Expression (4.2), the following expression can be obtained:

$$a_{Bi\_X}^2 + a_{Bi\_Z}^2 = g^2 \cos^2\alpha_i(\sin^2\beta_i + \cos^2\beta_i) \quad (5)$$

Further, the following expression is derived:

$$g\cos\alpha_i = \sqrt{a_{Bi\_X}^2 + a_{Bi\_Z}^2} \quad (6)$$

Furthermore, when Expression (4.2) is divided by Expression (6), the following expression can be obtained:

$$\alpha_i = \tan^{-1}\left(\frac{-a_{Bi\_Y}}{\sqrt{a_{Bi\_X}^2 + a_{Bi\_Z}^2}}\right) \quad (7)$$

As a result, the pitch angle $\alpha_i$ in the local coordinate system $C_i$ can be obtained. Moreover, when Expression (4.1) is divided by Expression (4.3), the following expression can be obtained:

$$\beta_i = \tan^{-1}\left(\frac{-a_{Bi\_X}}{a_{Bi\_Z}}\right) \quad (8)$$

The roll angle $\beta_i$ in the local coordinate system $C_i$ can be derived. As described above, based on measurement data in each acceleration sensor $A_i$, the pitch angle $\alpha_i$ and the roll angle $\beta_i$ in the local coordinate system $C_i$ can be calculated.

Figure 5:
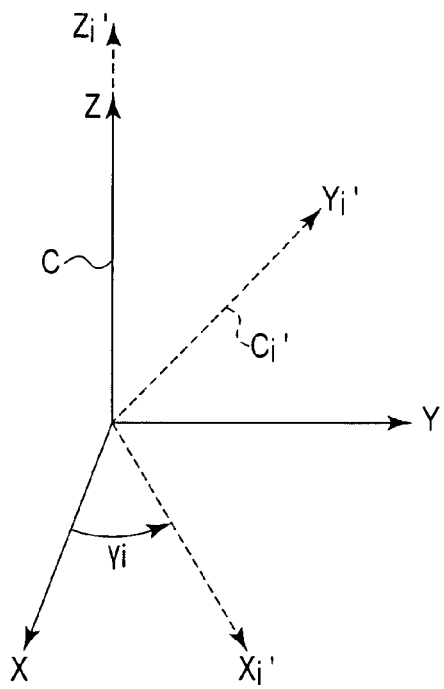
FIG. 5 is a schematic view showing a global coordinate system and a correction coordinate system of the endoscopic form detection device according to the first embodiment in comparison to each other.

Additionally, the second angle calculating section 36 calculates the yaw angle $\gamma_i$ in the local coordinate system $C_i$ of each sensor unit Si based on measurement data obtained by the geomagnetic sensor $B_i$ of each sensor unit $S_i$ (a step S103). Here, a corrected coordinate system $C'_i$ obtained by correcting the rotation from the global coordinate system C about the X axis and the rotation from the global coordinate system C about the Y axis in each local coordinate system $C_i$ is defined by using the pitch angle $\alpha_i$ and the roll angle $\beta_i$ calculated at the step S102. FIG. 5 is a view showing the global coordinate system C (indicated by a solid line in FIG. 5) and the corrected coordinate system $C'_i$ (indicated by a dotted line in FIG. 5). It is to be noted that the global coordinate system C and the corrected coordinate system $C'_i$ actually have origins provided at different positions, and FIG. 5 shows a state in which the origins are provided at the same position in order to compare both the coordinate systems. As shown in FIG. 5, the corrected coordinate system $C'_i$ obtained by correcting the rotation about the X axis and the rotation about the Y axis is a coordinate system obtained by rotating the global coordinate system C by the yaw angle $\gamma_i$ about the Z axis and has an $X'_i$ axis, a $Y'_i$ axis, and a $Z'_i$ axis. $X'_i$ directions and $Y'_i$ axis directions coincide with directions rotated by the yaw angle $\gamma i$ about the Z axis from the X axis directions and the Y axis directions in the global coordinate system C, respectively. $Z'_i$ axis directions coincide with the vertical directions, i.e., the Z axis directions in the global coordinate system C. Here, since the positive direction of the X axis directions in the global coordinate system C coincides with the magnetic north direction, a positive direction of the $X'_i$ directions is a direction rotated by the yaw angle $\gamma_i$ about the Z axis from the magnetic north direction.

It is assumed that an $X_i$ axis directions component, a $Y_i$ axis directions component, and a $Z_i$ axis directions component of a geomagnetic vector in the local coordinate system $C_i$ measured by the geomagnetic sensor $B_i$ are as follows:

$$\dot{m}_{obsi}=[M_{Xi}\, M_{Yi}\, M_{Zi}]^T \quad (9)$$

The corrected coordinate system $C'_i$ is a coordinate system obtained by correcting the rotation from the global coordinate system C about the X axis and the rotation from the global coordinate system C about the Y axis in the local coordinate system $C_i$. Therefore, based on $R_{xi}$ and $R_{yi}$ in Expression (1) and Expression (9), an $X'_i$ axis directions component, a $Y'_i$ axis directions component, and a $Z'_i$ axis directions component in the corrected coordinate system $C'_i$ of a geomagnetic vector measured by the geomagnetic sensor $B_i$ are as follows:

$$\dot{m}'_{obsi} = R_{Xi} R_{Yi} \dot{m}_{obsi} \quad (10.1)$$

$$= \begin{bmatrix} 1 & 0 & 0 \\ 0 & \cos\alpha_i & -\sin\alpha_i \\ 0 & \sin\alpha_i & \cos\alpha_i \end{bmatrix} \begin{bmatrix} \cos\beta_i & 0 & \sin\beta_i \\ 0 & 1 & 0 \\ -\sin\beta_i & 0 & \cos\beta_i \end{bmatrix} \begin{bmatrix} M_{Xi} \\ M_{Yi} \\ M_{Zi} \end{bmatrix}$$

$$= \begin{bmatrix} \cos\beta_i & 0 & \sin\beta_i \\ \sin\alpha_i\sin\beta_i & \cos\alpha_i & -\sin\alpha_i\cos\beta_i \\ -\cos\alpha_i\sin\beta_i & \sin\alpha_i & \cos\alpha_i\cos\beta_i \end{bmatrix} \begin{bmatrix} M_{Xi} \\ M_{Yi} \\ M_{Zi} \end{bmatrix}$$

$$\dot{m}'_{obsi} = [M'_{Xi}\ M'_{Yi}\ M'_{Zi}]^T \quad (10.2)$$

Based on Expression (10.1) and Expression (10.2), the following expressions can be obtained:

$$M_{Xi}' = M_{Xi}\cos\beta_i + M_{Zi}\sin\beta_i \quad (11.1)=$$

$$M_{Yi}' = M_{Yi}\cos\alpha_i + \sin\alpha_i(M_{Xi}\sin\beta_i - M_{Zi}\cos\beta_i) \quad (11.2)$$

A geomagnetic component on a horizontal plane (an $X'_i$-$Y'_i$ plane in the corrected coordinate system $C'_i$) perpendicular to the vertical directions directs the magnetic north direction. Therefore, based on Expression (11.2) and Expression (11.2), an angle $\theta_i$ from the $X'_i$ axis to the magnetic north direction can be obtained by using the $X'_i$ axis component and the $Y'_i$ axis component of the geomagnetic vector in the corrected coordinate system $C'_i$. That is, the following expression can be obtained:

$$\theta_i = \tan^{-1}(M_{Yi}'/M_{Xi}') \quad (12)$$

In regard to the angle $\theta_i$, a clockwise direction when seeing the $Z'_i$ axis (the Z axis) from a negative direction is determined to be positive. Here, the corrected coordinate system $C'_i$ is a coordinate system obtained by rotating the global coordinate system C the yaw angle $\gamma_i$ about the Z axis. Therefore, the angle $\theta_i$ obtained based on Expression (12) is the yaw angle $\gamma_i$ in the local coordinate system $C_i$ when the global coordinate system C is determined as a reference.

It is to be noted that, when one of the X axis directions in the global coordinate system C does not coincide with the magnetic north direction, the yaw angle $\gamma_i$ can be likewise obtained with reference to the magnetic north. An X axis directions component, a Y axis directions component, and a Z axis directions component of the geomagnetic vector in the global coordinate system C are determined as follows:

$$\dot{m}_{th} = [E_X E_Y E_Z]^T \qquad (13)$$

The X axis directions component, the Y axis directions component, and the Z axis directions component of the geomagnetic vector in the global coordinate system C can be obtained by using a geomagnetic sensor which is of the same type as the geomagnetic sensor $B_i$ to conduct the measurement in a state in which the X axis directions, the Y axis directions, and the Z axis directions in the global coordinate system C coincide with axis directions. Further, based on Expression (13), an angle $\theta$ from the X axis to the magnetic north direction is obtained by using the X axis component and the Y axis component of the geomagnetic vector in the global coordinate system C. That is, the following expression can be acquired:

$$\theta = \tan^{-1}(E_Y/E_X) \qquad (14)$$

Here, in regard to the angle $\theta$, the clockwise direction when the Z axis is seen from the negative direction is determined to be positive. The corrected coordinate system $C'_i$ is a coordinate system obtained by rotating the global coordinate system C by the yaw angle $\gamma_i$ about the Z axis. Therefore, based on Expression (12) and Expression (14), the following representation can be achieved:

$$\gamma_i = \theta - \theta_i \qquad (15)$$

As a result, when the global coordinate system C is determined as a reference the yaw angle $\gamma_i$ of the local coordinate system $C_i$ can be obtained.

As described above, based on the measurement data in each geomagnetic sensor $B_i$, the yaw angle $\gamma_i$ of each local coordinate system $C_i$ is calculated. Based on the calculated values of the posture angles $\alpha_i$, $\beta_i$, and $\gamma_i$, the posture detecting section 30 is configured to detect a posture of each sensor unit $S_i$.

Figure 6:
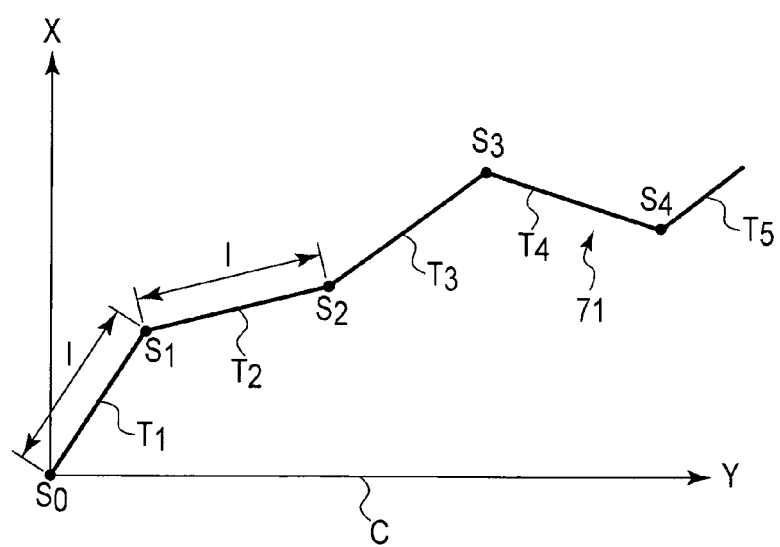
FIG. 6 is a schematic view showing a detected linear form detected by a linear form detecting section of the endoscopic form detection device according to the first embodiment.

As shown in FIG. 3, a linear form detecting section 40 is connected to the posture detecting section 30. FIG. 6 is a view showing a detected linear form 71 of the inserting section 11 of the endoscope 10 detected by the linear form detecting section 40 from the negative direction of the Z axis in the global coordinate C. As shown in FIG. 6, the linear form detecting section 40 is configured to detect the detected linear form 71 of the inserting section 11 on the assumption that a form between the respective sensor units $S_i$ is a linear link $T_j$ (j=, 1, 2, ... N) whose dimension is equal to the inter-sensor dimension 1 based on the posture of each sensor unit $S_i$ detected by the posture detecting section 30. Here, the kth link $T_k$ from the proximal end side is a link between the kth sensor unit $S_{k-1}$ from the proximal end side and the (K+1)th sensor unit $S_k$ from the proximal end side. The linear form detecting section 40 includes a link forming section 41 configured to form each link $T_j$, and a link position compensating section 42 configured to parallel translate each link $T_j$ formed by the link forming section 41 to compensate a position of the link $T_j$. The link position compensating section 42 is configured to parallel translate each link $T_j$ in such a manner that link boundaries between the link $T_j$ and adjacent links $T_{j-j}$ and $T_{j+j}$ become continuous.

A drawing section 45 is connected to the linear form detecting section 40. A display section 47 is connected to the drawing section 45. The detected linear form 71 of the inserting section 11 in the global coordinate system C detected by the linear form detecting section 40 is configured to be drawn by the drawing section 45. An operator can confirm the detected linear form 71 drawn by the drawing section 45 in the display section 47.

A method of detecting the detected linear form 71 of the inserting section 11 in the linear form detecting section 40 will now be described. As shown in FIG. 4, when detecting the detected linear form 71 of the inserting section 11, the link forming section 41 first forms each link $T_j$ having the linear form based on the values of the posture angles $\alpha_i$, $\beta_i$, and $\gamma_i$ calculated at the steps S102 and S103 (a step S104). Here, description will be given as to formation of a kth link $T_k$ from the proximal end side between a kth sensor unit $S_{k-1}$ from the proximal end side and a (k+1)th sensor unit $S_k$ from the proximal end side.

As represented by Expression (7), Expression (8), and Expression (12) (or Expression (15)), posture angles $\alpha_{k-1}$, $\beta_{k-1}$, and $\gamma_{k-1}$ in a local coordinate system $C_{k-1}$ (i.e., the link) are calculated at the steps S102 and S103. Each of the posture angles $\alpha_{k-1}$, $\beta_{k-1}$, and $\gamma_{k-1}$ and the inter-sensor dimension 1 which is between each of the sensor units $S_i$ can be used to obtain a coordinate $P'_k(l_{xk}, l_{yk}, l_{zk})$ of the sensor unit $S_k$ when the sensor unit $S_{k-1}$ is placed at the origin of the global coordinate system C. Here, the coordinate $P'_k$ is represented as follows:

$$\begin{aligned} i_k &= [\, l_{xk} \quad l_{yk} \quad l_{zk} \,]^T \\ &= l C^G_{Bk-1} e_{yk-1} \\ &= l \begin{bmatrix} -\sin\gamma_{k-1} \cdot \cos\alpha_{k-1} \\ \cos\gamma_{k-1} \cdot \cos\alpha_{k-1} \\ \sin\alpha_{k-1} \end{bmatrix} \end{aligned} \qquad (16.1)$$

$$e_{yk-1} = [\, 0 \quad 1 \quad 0 \,]^T \qquad (16.2)$$

In Expression (16.1) and Expression (16.2), $e_{yk-1}$ is a unit vector in $Y_{k-1}$ axis directions which are the longitudinal directions at the origin of the local coordinate system $C_{k-1}$. When the unit vector $e_{yk-1}$ is multiplied by a rotation matrix calculated by Expression (1), an X axis directions component, a Y axis directions component, and a Z axis directions component of the unit vector $e_{yk-1}$ in the global coordinate system C can be calculated, respectively. That is, $l_{xk}$, $l_{yk}$, and $l_{zk}$ are components obtained by dividing a vector having a magnitude 1 in the $Y_{k-1}$ axis directions in the local coordinate system $C_{k-1}$ to the X axis directions, the Y axis directions, and the Z axis directions in the global coordinate system C, respectively. The link $T_k$ is formed by linearly connecting the origin of the global coordinate system C with the coordinate $P'_k(l_{xk}, l_{yk}, l_{zk})$ calculated by Expression (16.1) and Expression (16.2).

It is to be noted that each link $T_j$ other than the link $T_k$ is likewise formed by the link forming section 41. That is, Expression (16.1) and Expression (16.2) are used to obtain a coordinate $P'_j(l_{xj}, l_{yj}, l_{zj})$ of the sensor unit $S_j$ on the distal end side (the side far from the origin of the global coordinate system C) of the link $T_j$ when the sensor unit $S_{j-1}$ on the proximal end side (the side close to the origin of the global coordinate system C) of the link $T_j$ is placed at the origin of the global coordinate system C. Further, the link $T_j$ is formed by linearly connecting the origin of the global coordinate system C to the coordinate $P'_j(l_{xj}, l_{yj}, l_{zj})$. That is, the link forming section 41 is configured to form the link $T_j$ on the assumption that the link $T_j$ is extended in the longitudinal directions at the center of the sensor unit $S_{j-1}$ on the proximal end side from the center of the sensor unit $S_{j-1}$ on the proximal end side (the side close to the origin of the global coordinate system C) to the center of the sensor unit $S_j$ on the distal end side (the side far from the origin of the global coordinate system C).

Furthermore, it is preferable for the inter-sensor dimension l to be approximately 50 mm. When the inter-sensor dimension l is increased, the number of the sensor units $S_i$ is reduced, thereby decreasing a cost. Moreover, when the inter-sensor dimension l is smaller than approximately 50 mm, an error when detecting a form of the inserting section 11 can be reduced even if the interval between the respective sensor units $S_i$ is assumed to be the linear link $T_j$ whose dimension is equal to the inter-sensor dimension l.

Figure 7:
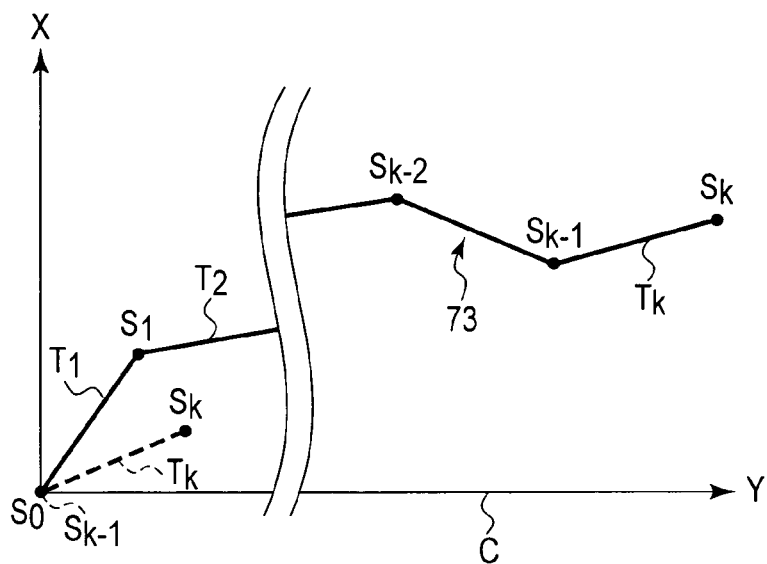
FIG. 7 is a schematic view explaining processing in a link position compensating section of the linear form detecting section according to the first embodiment.

Additionally, the link position compensating section 42 is configured to correct a position of the link $T_j$ by parallel translating each link $T_j$ formed by the link forming section 41 in such a manner that link boundaries between the link $T_j$ and adjacent links $T_{j-1}$ and $T_{j+1}$ become continuous (a step S105). FIG. 7 is a view explaining processing in the link position compensating section 42. Here, description will be given as to positional compensation of the kth link $T_k$ from the proximal end side between the kth sensor unit $S_{k-1}$ from the proximal end side and the (k+1)th sensor unit $S_k$ from the proximal end side.

As shown in FIG. 7, in a state before the link position compensating section 42 performs positional compensation of the link $T_k$, the positional compensation is completed from the first link to the link $T_{k-1}$ adjacent to the proximal end side of the link $T_k$, and a link positional compensation completed portion 73 is formed. When performing the positional compensation of the link $T_k$, the link position compensating section 42 parallel translates the link $T_k$ a distance from the origin to the distal end of the link positional compensation completed portion 73. That is, the link $T_k$ is parallel translated from a position indicated by a dotted line in FIG. 7 to a position indicated by a solid line in FIG. 7. As a result, a link boundary between the link $T_{k-1}$ and the link $T_k$ becomes continuous, and the position of the link $T_k$ is thereby compensated.

It is to be noted that a position of each link $T_j$ other than the link $T_k$ is likewise compensated. That is, when performing the positional compensation of the link $T_j$, the link position compensating section 42 is configured to parallel translate the link $T_j$ a distance from the origin to the distal end (the end on the side far from the origin of the global coordinate system C) of the link positional compensation completed portion 73. As a result, a link boundary between the link $T_j$ and a link $T_{j-1}$ adjacent to the proximal end side (the side close to the origin of the global coordinate system C) of the link $T_j$ becomes continuous, and a position of the link $T_j$ is thereby compensated. However, a position of a link $T_l$ is not compensated since a proximal end of the link $T_l$ is the origin of the global coordinate system C.

Figure 8:
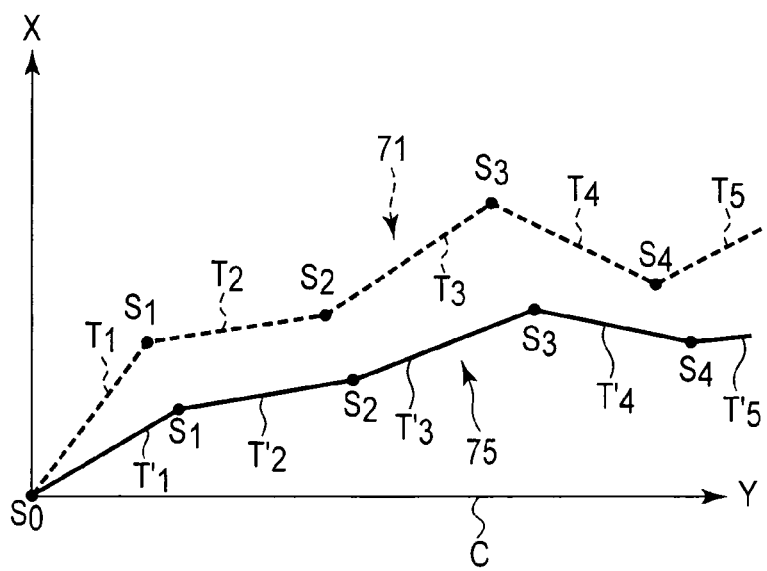
FIG. 8 is a schematic view showing a corrected form subjected to form correction by a form correcting section in the endoscopic form detection device according to the first embodiment.

As shown in FIG. 3, the linear form detecting section 40 is connected to a form correcting section 50. The form correcting section 50 is configured to compensate a position (a state) of each sensor unit $S_i$ by using a particle filter to correct the detected linear form 71 detected by the linear form detecting section 40. FIG. 8 is a view showing a corrected form 75 of the inserting section 11 of the endoscope 10 corrected by the form correcting section 50 from the positive direction of the Z axis in the global coordinate C. As shown in FIG. 8, the detected liner form 71 indicated by a dotted line in FIG. 8 is corrected into the corrected form 75 by the form correcting section 50. When a position of each sensor unit $S_i$ is compensated, the form of each link $T_j$ is corrected to determine a corrected link (a corrected inter-sensor element) $T'_j$. The corrected form 75 is constituted of each corrected link $T'_j$.

The form correcting section 50 includes a form correction sequentially implementing section 51 configured to correct a form of each link $T_j$ in the order starting from the link $T_j$ on the proximal end side (the side close to the origin of the global coordinate system C) to form the corrected link $T'_j$, and a form correction controlling section 52 configured to control the form correction sequentially implementing section 51 to perform the form correction with respect all the links $T_j$. Further, the form correcting section 50 includes an uncorrected link position compensating section 53 configured to parallel translate a correction uncompleted portion 79 constituted of a link $T_j$ that is not subjected to the form correction (an uncorrected link) to correct a position every time the form correction of one link $T_j$ is performed by the form correction sequentially implementing section 51. The uncorrected link position compensating section 53 is configured to parallel translate the correction uncompleted portion 79 in such a manner that a boundary between the correction uncompleted portion 79 and a correction completed portion 77 constituted of the corrected link $T'_j$ formed by the form correction becomes continuous.

As shown in FIG. 3, the form correction sequentially implementing section 51 includes a sensor position compensating section (a sensor state compensating section) 55 configured to compensate a position (a state) of a sensor unit (a state compensation target sensor) $S_j$ on the distal end side (the side far from the origin of the global coordinate system C) of a link $T_j$ as a correction target (a correction target link), and a corrected link forming section (a corrected inter-sensor element forming section) 57 configured to form a corrected link $T'_j$ based on the position of the sensor unit $S_j$ compensated by the sensor position compensating section 55.

Furthermore, the form correction sequentially implementing section 51 includes a sensor position estimating section (a sensor state estimating section) 61 configured to estimate a position of the sensor unit $S_j$ on the distal end side of the link $T_j$ as the correction target by using the particle filter. The sensor position estimating section 61 is configured to carry out the first positional estimation of the sensor unit $S_j$ based on an initial position (an initial state) placed at the distal end of the link $T_j$. Moreover, the sensor position estimating section 61 is configured to perform the second positional estimation of the sensor unit $S_j$ based on a result of the first estimation. That is, the sensor position estimating section 61 is configured to carry out the positional estimation of the sensor unit $S_j$ based on the initial position or an estimation result of the previous estimation by using the particle filter. Additionally, the form correction sequentially implementing section 51 includes a position estimation controlling section (a state estimation controlling section) 62 configured to control the sensor position estimating section 61 in such a manner that the positional estimation of the sensor unit $S_j$ can be effected for a predetermined number of times.

The sensor position estimating section 61 includes a particle dispersing section 63, a particle moving section 65, a weight calculating section 67, and a sensor position observing section (a sensor state observing section) 69. Details of the particle dispersing section 63, the particle moving section 65, the weight calculating section 67, and the sensor position observing section 69 will be described later.

The form correcting section 50 is connected with the drawing section 45. The drawing section 45 is configured to draw the corrected form 75 of the inserting section 11 corrected by the form correcting section 50 in the global coordinate system C. An operator can confirm the corrected form 75 drawn by the drawing section 45 in the display section 47.

A method of using the form correcting section 50 to correct the detected linear form 71 detected by the linear form detecting section 40 will now be described. As shown in FIG. 4, the form correcting section 50 is configured to compensate a position of each sensor unit $S_i$ by using the particle filter and to correct the detected linear form 71 detected by the linear form detecting section 40 (a step S106). As described above, when the inter-sensor dimensional is smaller than approximately 50 mm, an error when detecting a form of the inserting section 11 can be reduced even if an interval between the respective sensor units $S_i$ is assumed to be a linear link $T_j$ whose dimension is equal to the inter-sensor dimension l. However, measurement data of each sensor unit $S_i$ actually has an error due to noise and the like, and the inserting section 11 of the endoscope 10 when inserted into a body cavity has a curved form. Therefore, the form of the inserting section 11 is not restricted to a linear link form extended in the longitudinal directions at the center of a sensor unit $S_{j-1}$ on the proximal end side from the center of a sensor unit $S_{j-1}$ on the proximal end side to the center of a sensor unit $S_j$ on the distal end side. Therefore, performing the form correction of the detected linear form 71 is important.

When compensating a position of each sensor unit $S_i$ and correcting the detected linear shape 71, the form correction sequential implementing section 51 sequentially carries out the form correction in the order starting from the link $T_j$ on the proximal end side (the side close to the origin of the global coordinate system C) in accordance with each link $T_j$, thereby forming a corrected link $T'_1$. Here, a method of performing the form correction of the link $T_j$ by the form correction sequentially implementing section 51 will now be described. Here, description will be given as to the form correction of a kth link $T_k$ from the proximal end side between a kth sensor unit $S_{k-1}$ from the proximal end side and a (k+1)th sensor unit $S_k$ from the proximal end side.

Figure 9:
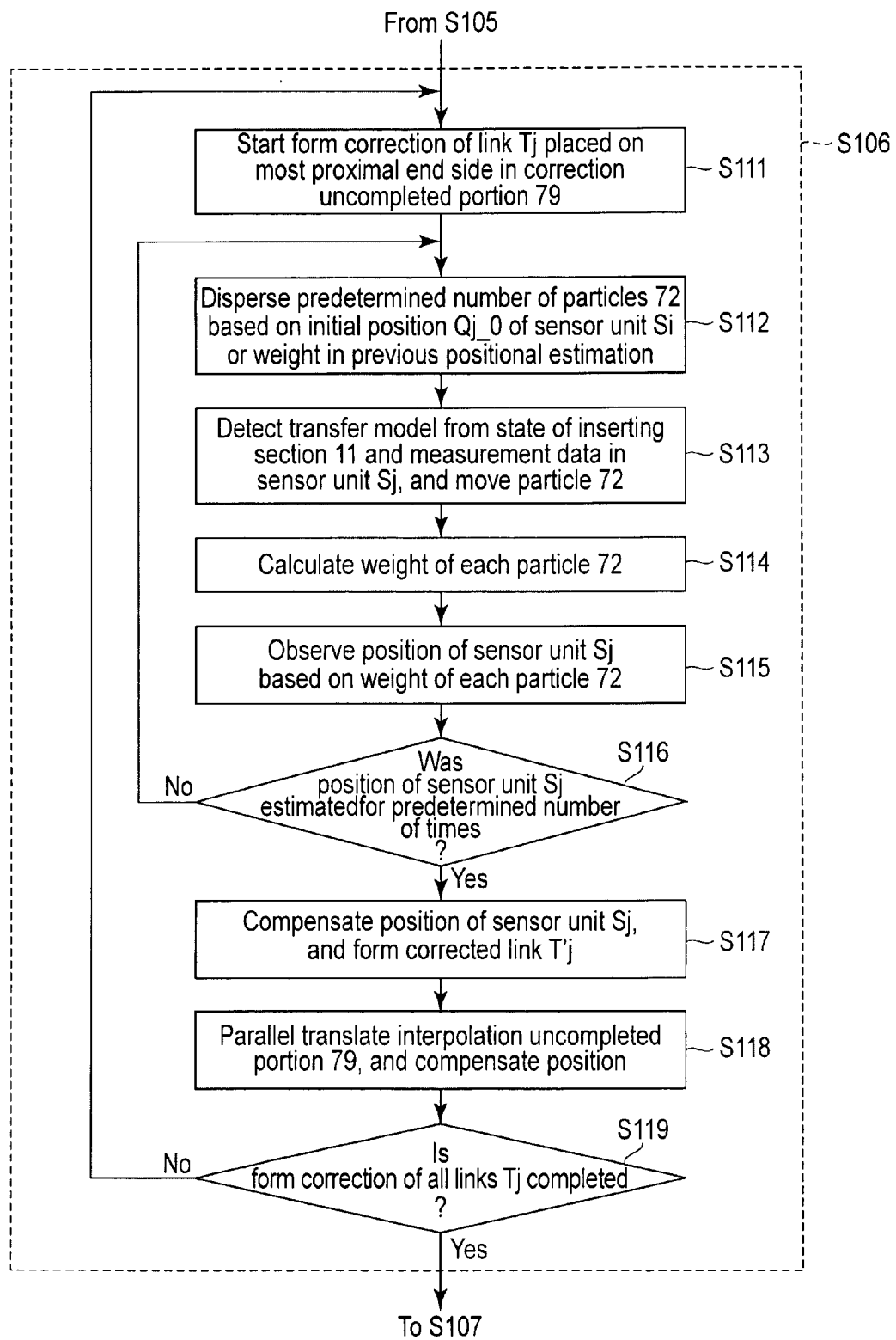
FIG. 9 is a flowchart showing a method of correcting a detected linear form by the form correcting section according to the first embodiment.
Figure 10:
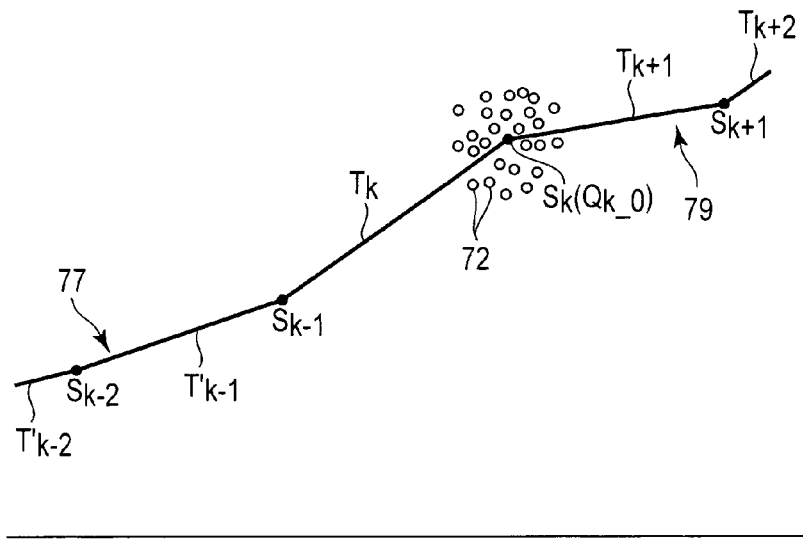
FIG. 10 is a schematic view showing a dispersed state of respective particles dispersed by a particle dispersing section at the time of a first observation in a sensor position observing section of the form correcting section according to the first embodiment.

FIG. 9 is a flowchart showing a method of correcting a form of the detected linear form 71 by the form correcting section 50. FIG. 10 to FIG. 15 are views explaining processing in the form correction sequentially implementing section 51. As shown in FIG. 10, in a state before the form correction of the link $T_k$ is carried out by the form correction sequentially implementing section 51, the form correction from the first link to the link $T_{k-1}$ is completed, thereby forming a correction completed portion 77. The correction completed portion 77 is constituted of corrected links $T'_1$ to $T'_{k-1}$. Further, a correction uncompleted portion 79 constituted of the links $T_k$ to $T_N$ is also formed. At this time, a boundary between the correction completed portion 77 and the correction uncompleted portion 79 is continuous, and the sensor unit $S_k$ is placed at a point $Q_{k\_0}$ in the global coordinate system C.

In this state, the form correction sequentially implementing section 51 starts the form correction of the link (a correction target link) $T_k$ placed on the most proximal end side in the correction uncompleted portion 79 (a step S111). That is, the form correction controlling section 52 controls the form correction sequentially implementing section 51 to perform the form correction of the link $T_k$.

When performing the form correction of the link $T_k$ by the form correction sequentially implementing section 51, the sensor position estimating section 61 first uses the particle filter to estimate a position of the sensor unit (a state compensation target sensor) $S_k$ on the distal end side of the link $T_k$ based on the initial position ($Q_{k\_0}$) placed at the distal end of the link $T_k$. As shown in FIG. 9 and FIG. 10, when estimating the position of the sensor unit $S_k$ based on the initial position, the particle dispersing section 63 first disperses a predetermined number (A in this embodiment) of particles 72 around the initial position $Q_{k\_0}$ of the sensor unit $S_k$ on the distal end side of the link $T_k$ (a step S112). Here, the initial position of the sensor unit $S_k$ (i.e., a state vector in the particle filter) is determined as $Q_{k\_0}(q_{xk\_0}, q_{yk\_0}, q_{zk\_0})$, and variance of an error in the initial position $Q_{k\_0}$ is determined as ($\delta_x, \delta_y, \delta_z$). When obtaining $\delta_x, \delta_y, \delta_z$, variance of errors in posture angles $\alpha_{k-1}, \beta_{k-1}$, and $\gamma_{k-1}$ of the sensor unit $S_{k-1}$ from variance of an error in measurement data of each sensor unit $S_i$ generated due to noise and the like by using Expression (1) to Expression (15). Furthermore, the variance $\delta_x, \delta_y, \delta_z$ of the error in the initial position $Q_{k\_0}$ of the sensor unit $S_k$ is obtained from the variance of the error in the posture angles $\alpha_{k-1}, \beta_{k-1}$ and $\gamma_{k-1}$ by using Expression (16). Particles 72 are uniformly dispersed in the range obtained by adding the variance $\delta_x, \delta_y, \delta_z$ of the error to the initial position $Q_{k\_0}$ of the sensor unit $S_k$. That is, assuming that a position of each particle 72 in the global coordinate system C is $Q_{K\_1}^a(q_{xk\_1}^a, q_{yk\_1}^a, q_{zk\_1}^a)$ (a=1, 2, ..., A), the particles 72 are uniformly dispersed in the following range:

$$q_{xk\_0} - \delta_x \leq q_{xk\_1}^a \leq q_{xk\_0} + \delta_x \quad (17.1)$$

$$q_{yk\_0} - \delta_y \leq q_{yk\_1}^a \leq q_{yk\_0} + \delta_y \quad (17.2)$$

$$q_{zk\_0} - \delta_z \leq q_{zk\_1}^a \leq q_{zk\_0} + \delta_z \quad (17.3)$$

That is, noise of the system is assumed as white noise. It is to be noted that the dispersion range of the particles may be empirically determined, but estimation accuracy is deteriorated when the dispersion range is too large. When the individual particles 72 are first dispersed, an initial weight $w_{k\_0}^a$ is provided to each particle 72 in advance. The weight $w_{k\_0}^a$ is provided as fixed 1/A to each particle 72, for example. Here, the particles 72 represent a probability density function of the state vector by using A discrete hypotheses, and each particle 72 has the weight $w_{k\_0}^a$ proportional to the probability. That is, in the particle filter, the plurality of (A in this embodiment) particles 72 are used to estimate the probability density function of the state vector.

Furthermore, the particle moving section 65 is configured to detect a transfer model of each particle 72 based on a state of the inserting section 11 (a moving state, a bent state, and others) and measurement data in the sensor unit $S_k$. Moreover, the particle moving section 65 is configured to select each particle 72 based on the probability proportional to the weight $w_{k\_0}^a$ and to move each particle 72 based on the detected transfer model (a step S113). Each particle 72 is moved from a pre-movement particle position to a post-movement particle position by the particle moving section 65. However, in this embodiment, since the inserting section 11 is in the stationary state and curve interpolation between the respective sensor units $S_i$ is not performed, the particles 72 are not moved.

Moreover, the weight calculating section 67 is configured to calculate a weight $w_{k\_1}^a$ of each particle 72 (a step S114). That is, the weight of each particle 72 is updated from $w_{k\_0}^a$ to $w_{k\_1}^a$. The weight calculating section 67 first calculates likelihood $v_{k\_1}^a$ for evaluating how likely each particle 72 is. The likelihood represents how likely the sensor unit $S_k$ is placed at the post-movement particle position to which each particle 72 is moved by the particle moving section 65. The likelihood is as follows:

$$v_{k\_1}^a = h(b_{k\_1}^a) + g(\phi_{k\_1}^a) \quad (18)$$

Figure 11:
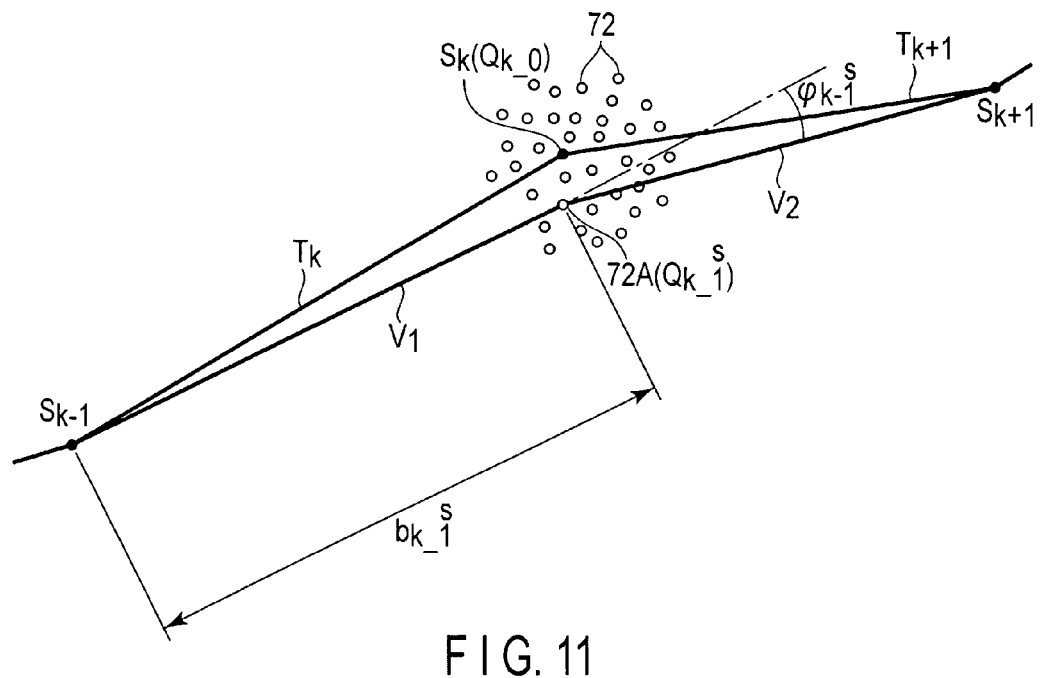
FIG. 11 is a schematic view explaining processing in a weight calculating section of the sensor position observing section of the form correcting section according to the first embodiment.

$b_{k\_1}^a$ is a dimension of a line segment between the sensor unit $S_{k-1}$ after the positional compensation and each particle 72 in the global coordinate system C. For example, as shown in FIG. 11, a dimension of a line segment between the sensor unit $S_{k-1}$ and a particle 72A (a particle provided at a position $Q_{k\_1}^s$ in the global coordinate system C) is $b_{k\_1}^s$. Here, for example, a function $h(b_{k\_1}^a)$ is assumed as follows:

$$h(b_{k\_1}^a) = \exp(-|b_{k\_1}^a - b_0|) \quad (19)$$

$b_0$ is assumed as the inter-sensor dimension l of each sensor unit $S_i$. Based on Expression (19), the function $h(b_{k\_1}^a)$ increases and the likelihood becomes large as a difference between the inter-sensor dimension l and a dimension of a line segment between the sensor unit $S_{k-1}$ after the positional compensation and the particle 72 decreases. Contrarily, the function $h(b_{k\_1}^a)$ decreases and the likelihood becomes small as the difference between the inter-sensor dimension l and the dimension of the line segment between the sensor unit $S_{k-1}$ after the positional compensation and the particle 72 increases. $\phi_{k\_1}^a$ is an angle formed between a vector V1 from the sensor unit $S_{k-1}$ after the positional compensation to each particle 72 and a vector V2 from each particle 72 to the sensor unit $S_{k+1}$ before the positional compensation. For example, as shown in FIG. 11, in the case of the particle 72A (the particle provided at the position $Q_{k\_1}^s$ in the global coordinate system C), the angle formed between the vector V1 and the vector V2 is $\phi_{k\_1}^s$. Here, for example, a function $g(\phi_{k\_1}^a)$ is assumed as follows:

$$g(\varphi_{k\_1}^a) = \frac{1}{1 + c \cdot \exp(|\varphi_{k\_1}^a| - \Pi/2)} \quad (c > 0) \quad (20)$$

Here, c is a constant, and it is, e.g., 4. Based on Expression (20), if the angle formed between the vectors V1 and V2 falls within the range of 0 degrees to ±90 degrees, the function $g(\phi_{k\_1}^a)$ increases and the likelihood becomes large. Contrarily, in the case of any other angle, the function $g(\phi_{k\_1}^a)$ decreases, and the likelihood becomes small. If the inter-sensor dimension l of each sensor unit $S_i$ is 50 mm, the angle $\phi_{k\_1}^a$ can actually fall within the range of 0 degrees to ±90 degrees. This can be readily conceived from a state in which a resin tube, which has a diameter of 10 mm substantially equal to a diameter of the inserting section 11 of the endoscope 10, is bent. Since the range of the angle $\phi_{k\_1}^a$ differs depending on a product or a position of the inserting section, it is desirable to adjust this range in accordance with the product and/or the position of the inserting section.

Further, the weight $w_{k\_1}^a$ is calculated from the likelihood of each particle 72. The weight of each particle 72 is as follows:

$$w_{k\_1}^a = \frac{v_{k\_1}^a}{\sum_{a=1}^{A} v_{k\_1}^a} \quad (21)$$

That is, the weight is a value obtained by standardizing the likelihood of each particle 72 with a total of the respective pieces of likelihood being determined as 1. As described above, the weight of each particle 72 is calculated.

Furthermore, the sensor position observing section 69 is configured to observe a position of the sensor unit $S_k$ based on the weight of each particle 72 calculated by the weight calculating section 67 (a step S115). At this moment, as shown in FIG. 12, the sensor position observing section 69 calculates a weighted mean of the pre-movement particle positions of the respective particles 72 before being moved by the particle moving section 65, and it determines the calculated position as a pre-movement sensor position $Q'_{k\_1}$. Moreover, based on the transfer model used by the particle moving section 65 when moving each particle 72, movement from the pre-movement sensor position $Q'_{k\_1}$ to the post-movement sensor position $Q_{k\_1}$ is carried out, and the post-movement sensor position $Q_{k\_1}$ is estimated as a position of the sensor unit $S_k$. It is to be noted that, in this embodiment, each particle 72 is not moved by the particle moving section 65, and hence the pre-movement sensor position $Q'_{k\_1}$ is equal to the post-movement sensor position $Q_{k\_1}$.

Additionally, the position estimation controlling section 62 is configured to judge whether estimation of the position of the sensor unit $S_k$ has been carried out for a predetermined number of times (M times in this embodiment) (a step S116). Under existing circumstances, since the estimation of the position of the sensor unit $S_k$ has been performed only once (the step S116—No), the sensor position estimating section 61 is controlled to a state in which the estimation of the position of the sensor unit $S_k$ is carried out one more time by the position estimation controlling section 62. At this time, the sensor position estimating section 61 is configured to carry out the estimation of the position of the sensor unit $S_k$ based on a first estimation result. Likewise, for example, in the t-th estimation of the position, the position of the sensor unit $S_k$ is estimated based on a (t−1)th estimation result. That is, in the second or subsequent estimation of the position, the sensor position estimating section 61 is configured to estimate the position of the sensor unit $S_k$ based on an estimation result of the previous estimation of the position.

Moreover, the processing returns to the step S112 where the particle dispersing section 63 disperses the predetermined number (A in this embodiment) of the particles 72 (the step S112). In the second estimation of the position, the particles 72 are dispersed based on the weight of each particle 72 calculated by the weight calculating section 67 at the time of the first estimation of the position. Likewise, for example, in the t-th estimation of the position, the particles 72 are dispersed based on the weight of each particle 72 calculated by the weight calculating section 67 at the time of the (t−1)th estimation of the position. That is, in the second or subsequent estimation of position, the particle dispersing section 63 is configured to disperse the particles 72 based on the weight of each particle 72 calculated by the weight calculating section 67 at the time of the previous estimation of the position. That is, the particle dispersing section 63 is a weight-based dispersing section configured to disperse the particles 72 based on a weight of each particle 72. As a result, as shown in FIG. 13A and FIG. 13B, for example, the number of the particles 72 to be dispersed is increased around the pre-movement particle positions of the particles 72 having large weights calculated in the previous estimation of the position (the range indicated by G1 in FIG. 13A and FIG. 13B). On the other hand, the number of the particles 72 to be dispersed is reduced around the pre-movement particle positions of the particles 72 having small weights calculated in the previous estimation of the position (the range indicated by G2 in FIG. 13A and FIG. 13B). It is to be noted that FIG. 13A shows the pre-movement particle positions of the particles 72 dispersed in the previous estimation of the position before being moved by the particle moving section 65, and FIG. 13B shows the pre-movement particle positions of the current particles.

Further, in the second or subsequent positional estimation, likewise, the particle moving section 65 is configured to move each particle 72 based on the transfer model used in the first estimation (a step S113). As a result, each particle 72 moves from the pre-movement particle position to the post-movement particle position.

Furthermore, the weight calculating section 67 uses the same expressions as Expression (18) to Expression (20) to calculate likelihood for evaluating how likely each particle 72 is. The likelihood represents how likely the sensor unit $S_k$ is placed at the post-movement particle position to which each particle 72 has been moved by the particle moving section 65. Further, a weight of each particle 72 is calculated from the likelihood by using the same expression as Expression (21) (a step S114). Here, for example, in the t-th positional estimation, likelihood $v_{k\_t}{}^a$ and weights $w_{k\_t}{}^a, b_{k\_t}{}^a, \phi_{k\_t}{}^a$ are used for calculation in place of the likelihood $v_{k\_1}{}^a$ and weights $w_{k\_1}{}^a, b_{k\_1}{}^a, \phi_{k\_1}{}^a$ in Expression (18) to Expression (21).

Moreover, the sensor position observing section 69 is configured to estimate the position of the sensor unit $S_k$ based on the weight of each particle 72 calculated by the weight calculating section 67 (a step S115). At this time, the sensor position observing section 69 calculates a weighted mean of the pre-movement particle positions of the respective particles 72 before being moved by the particle moving section 65 and determines the calculated position as a pre-movement sensor position. Additionally, based on the transfer model used by the particle moving section 65 to move each particle 72, movement from the pre-movement sensor position to a post-movement sensor position is performed, and the post-movement sensor position is estimated as the position of the sensor unit $S_k$. For example, in the t-th positional estimation, the pre-movement sensor position $Q'_{k\_t}$ is calculated from the weighted mean of the respective particles 72, and the movement from the pre-movement sensor position $Q'_{k\_t}$ to the post-movement sensor position $Q_{k\_t}$ is effected based on the movement using the transfer model.

Further, the positional estimation controlling section 62 is configured to judge whether the position of the sensor unit $S_k$ has been estimated for a predetermined number of times (M in this embodiment) (a step S116). When the position of the sensor unit $S_k$ has not been estimated for the predetermined number of times (the step S116—No), the position estimation controlling section 62 controls the sensor position estimating section 61 to estimate the position of the sensor unit $S_k$ one more time, and the step S112 to the step S115 are performed one more time. When the position of the sensor unit $S_k$ has been estimated for the predetermined number of times (the step S116—Yes), the processing advances to the next step.

Figure 14:
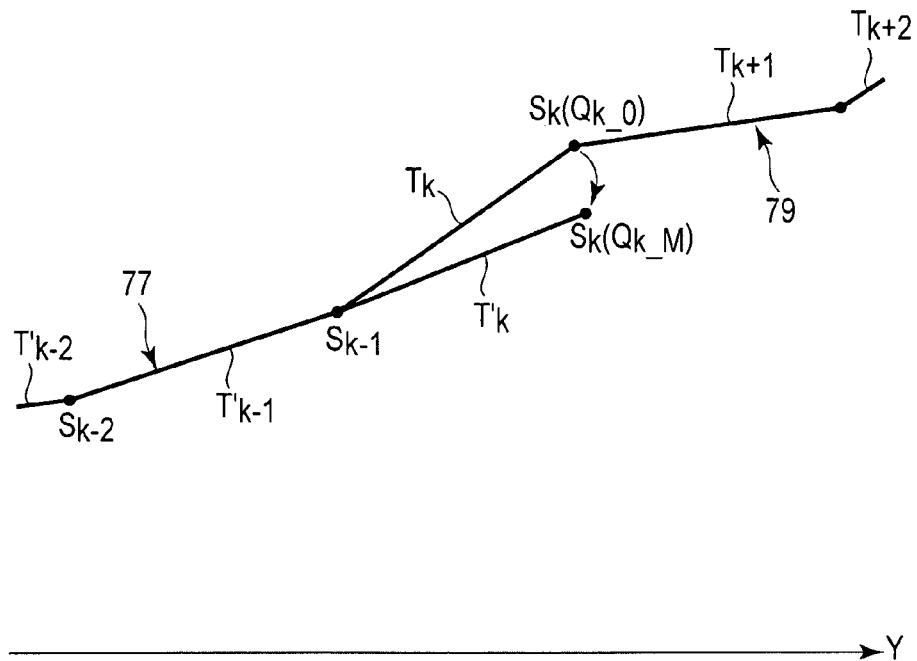
FIG. 14 is a schematic view explaining processing in a sensor position compensating section and a corrected link forming section of the form correcting section according to the first embodiment.

As shown in FIG. 14, after estimating the position of the sensor unit $S_k$ for the predetermined number of times, the sensor position compensating section 55 is configured to compensate the position of the sensor unit (a state compensation target sensor) $S_k$ on the distal end side of the link as a correction target (a correction target link) $T_k$ (a step S117). The sensor position compensating section 55 is configured to compensate the position of the sensor unit $S_k$ from the initial position $(Q_{k\_0})$ provided at the distal end of the link $T_k$ to a post-movement sensor position $Q_{k\_M}$ of the sensor unit $S_k$ estimated in the last (the mth in this embodiment) positional estimation performed by the sensor position observing section 61. Moreover, the corrected link forming section 57 forms a corrected link $T'_k$ based on the position of the sensor unit $S_k$ compensated by the sensor position compensating section 55 (a step S117). Here, a line segment connecting the sensor unit $S_{k-1}$ after the position compensation to the post-movement sensor position $Q_{k\_M}$ of the sensor unit $S_k$ is the corrected link $T'_k$. Because of the movement of the position of the sensor unit $S_k$, a boundary between the correction completed portion 77 and the correction uncompleted portion 79, which is continuous before the form of the link $T_k$ is corrected by the form correction sequentially implementing section 51, becomes discontinuous. That is, the corrected link $T'_k$ and the link $T_{k+1}$ become discontinuous.

It is to be noted that a form of each link $T_j$ other than the link $T_k$ is likewise corrected by the form correction sequentially implementing section 51. That is, when the form correction of the link (a correction target link) $T_j$ begins (a step S111), the sensor position estimating section 61 uses the particle filter to estimate a position of the sensor unit (a state compensation target sensor) $S_j$ on the distal end side (the side far from the origin of the global coordinate C) of the link $T_j$ as a correction target. When estimating the position of the sensor unit $S_j$, the particle dispersing section 63 first disperses a predetermined number of particles 72 based on an initial position $Q_{j\_0}$ of the sensor unit $S_j$ or a weight of each particle 72 calculated by the weight calculating section 67 in the previous positional estimation (the step S112). Additionally, the particle moving section 65 is configured to detect the above-described transfer model and to move each particle 72 based on the transfer model (the step S113). As a result, each particle 72 moves from the pre-movement particle position to the post-movement particle position.

Further, the weight calculating section 67 is configured to calculate likelihood for evaluating how likely each particle 72 is by using the same expressions as Expression (18) to Expression (20). Based on the likelihood, it is possible to detect how likely the sensor unit $S_j$ is placed at the post-movement particle position to which each particle 72 has been moved by the particle moving section 65. Furthermore, a weight of each particle 72 is calculated from the likelihood by using the same expression as Expression (21) (the step S114). Here, since the form of the link $T_j$ is corrected, for example, in the t-th positional estimation, likelihood $v_{j\_t}{}^a$ and weights $w_{j\_t}{}^a, b_{j\_t}{}^a,$ and $\phi_{j\_t}{}^a$ are used for calculation in place of the likelihood $v_{k\_1}{}^a$ and the weights $w_{k\_1}{}^a, b_{k\_1}{}^a, \phi_{k\_1}{}^a$ in Expression (18) to Expression (21). Moreover, the sensor position observing section 69 is configured to observe the position of the sensor unit $S_j$ based on the weight of each particle 72 calculated by the weight calculating section 67 (the step S115). For example, in the t-th positional estimation, a pre-movement sensor position $Q'_{j\_t}$ is calculated from the weighted mean of the respective particles 72, and the movement from the pre-movement sensor position $Q'_{j\_t}$ to the post-movement sensor position $Q_{j\_t}$ is carried out based on the movement using the transfer model. Additionally, the post-movement sensor position $Q_{j\_t}$ is estimated as the position of the sensor unit $S_j$.

Further, the position estimation controlling section 62 is configured to judge whether the position of the sensor unit $S_j$ has been estimated for the predetermined number of times (M times in this embodiment) (the step S116). When the position of the sensor unit $S_j$ has not been estimated for the predetermined number of times (the step S116—No), the sensor position estimating section 61 is controlled by the position estimation controlling section 62 to estimate the position of the sensor unit $S_j$ for the predetermined number of times, and the steps S112 to S115 are carried out one more time. When the position of the sensor unit $S_j$ has been estimated for the predetermined number of times (the step S116—Yes), the processing advances to the next step.

After the sensor position estimating section 61 has estimated the position of the sensor unit $S_j$ for the predetermined number of times, the sensor position compensating section 55 is configured to compensate the position of the sensor unit (a state compensation target sensor) $S_j$ on the distal end side (the side far from the origin of the global coordinate system C) of the link as a correction target (a correction target link) $T_j$ (the step S117). The sensor position compensating section 55 is configured to compensate the position of the sensor unit $S_j$ from the initial position ($Q_{j\_0}$) provided at the distal end (an end on the far side from the origin of the global coordinate system) of the link $T_j$ to a post-movement sensor position $Q_{j\_M}$ of the sensor unit $S_j$ estimated in the last (the mth in this embodiment) positional estimation performed by the sensor position observing section 61. Moreover, the corrected link forming section 57 is configured to form a corrected link $T'_j$ based on the position of the sensor unit $S_j$ compensated by the sensor position compensating section 55 (the step S117). Here, a line segment connecting the sensor unit $S_{j-1}$ after the position compensation to the post-movement sensor position $Q_{j\_M}$ of the sensor unit $S_j$ is the corrected link $T'_j$.

Figure 15:
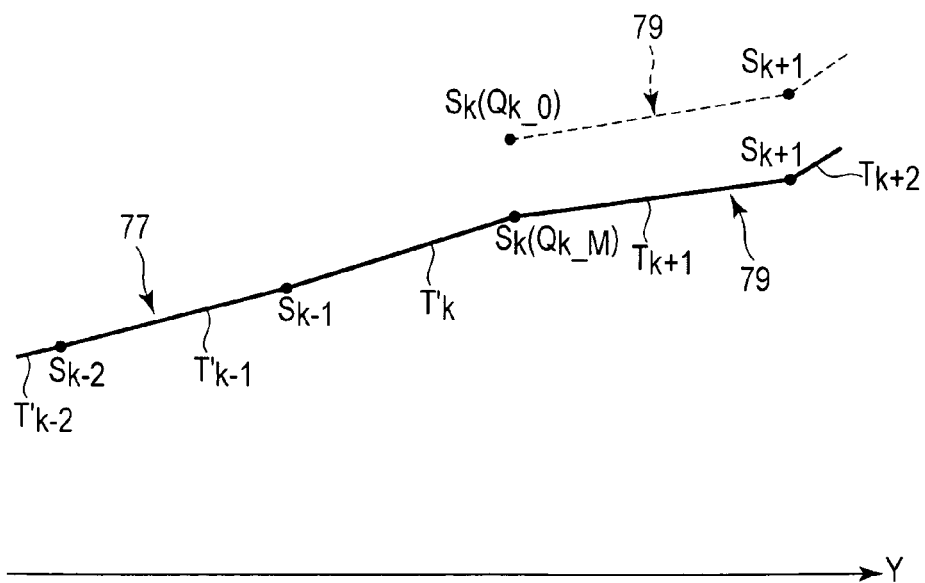
FIG. 15 is a schematic view explaining processing in an uncorrected link position compensating section of the form correcting section according to the first embodiment.

FIG. 15 is a view explaining processing in the uncorrected link position compensating section 53. As shown in FIG. 15, the form correction sequentially implementing section 51 corrects the form of the link $T_k$, and the correction completed portion 77 whose form has been completely corrected and the correction uncompleted portion 79 whose form has not been corrected are formed in a state after forming the corrected link $T'_k$. The correction completed portion 77 is constituted of the corrected links $T'_1$ to $T'_k$, and the correction uncompleted portion 79 is constituted of the links $T_{k+1}$ to $T_N$. At this time, as described above, since the position of the sensor unit $S_k$ moves from the point $Q_{k\_0}$ to the point $Q_{k\_M}$ due to the form correction of the link $T_k$, the boundary between the correction completed portion 77 and the correction uncompleted portion 79 is discontinuous. In this state, the uncorrected link position compensating section 53 is configured to parallel translate the correction uncompleted portion 79 in such a manner that the boundary between the correction uncompleted portion 79 and the correction completed portion 77 becomes continuous, thereby compensating the position of the correction uncompleted portion 79 (a step S118). That is, the correction uncompleted portion 79 is translated from a position indicated by a dotted line in FIG. 15 to a position indicated by a solid line in FIG. 15.

It is to be noted that, in regard to each link $T_j$ other than the link $T_k$, the uncorrected link position compensating section 53 likewise compensates the position of the correction uncompleted portion 79. That is, after the form correction sequentially implementing section 51 corrects the form of the link $T_j$, the boundary between the correction completed portion 77 and the correction uncompleted portion 79 is discontinuous. In this state, the uncorrected link position compensating section 53 is configured to parallel translate the correction uncompleted portion 79 in such a manner that the correction uncompleted portion 79 becomes continuous with the correction completed portion 77, thereby compensating the position of the correction uncompleted portion 79 (the step S118). The uncorrected link position compensating section 53 is configured to compensate the position of the correction uncompleted portion 79 every time a form of one link $T_j$ is corrected by the form correction sequentially implementing section 51.

Furthermore, as shown in FIG. 9, the form correction controlling section 52 is configured to confirm whether the form correction of all the links $T_j$ has been completed (a step S119). If the form correction of all the links $T_j$ has been completed, the corrected form 75 of the inserting section 11 is formed, and the processing advances to the next step (the step S119—Yes). If the form correction of all the links $T_j$ has not been completed, the processing returns to the step S111 (the step S119—No), and the form correction sequentially implementing section 51 corrects a form of a link (a correction target link) $T_j$ placed on the most proximal side (the side close to the origin of the global coordinate system C) in the correction uncompleted portion 79. That is, the steps S111 to S118 are repeated until the form correction of all the links $T_j$ is completed.

Therefore, the endoscopic form detection device 1 and the form detection method of the inserting section 11 of the endoscope 10 using the endoscopic form detection device 1 exercise the following effects. That is, in the endoscopic form detection device 1, the posture detecting section 30 is configured to detect a posture of each sensor unit $S_i$ from measurement data of each sensor unit $S_i$, and the linear form detecting section 40 is configured to detect the detected linear form 71 of the inserting section 11 of the endoscope 10 from the posture of each sensor unit $S_i$. Further, the form correcting section 50 is configured to compensate a position of each sensor unit $S_i$ by using the particle filter and to correct the detected linear form 71 detected by the linear form detecting section 40. Furthermore, the corrected form 75 of the inserting section 11 is formed. As described above, since the corrected form 75 of the inserting section 11 is detected from the measurement data of each sensor unit $S_i$ arranged in the inserting section 11 configured to be inserted into a body cavity at the time of observation, a sense coil and others do not have to be provided outside a body. Therefore, miniaturization and simplification of the endoscopic form detection device 1 can be realized.

Moreover, in the endoscopic form detection device 1, the form correcting section 50 is configured to compensate a position of each sensor unit $S_i$ by using the particle filter and to correct the detected linear form 71. In the form correcting section 50, the sensor position estimating section 61 of the form correction sequentially implementing section 51 is configured to estimate each sensor unit $S_i$ for a predetermined number of times. When estimating each sensor unit $S_i$, the weight calculating section 67 is configured to calculate a weight of each particle 72. Additionally, the sensor position observing section 69 is configured to observe the position of each sensor unit $S_i$ based on the weight of each particle 72 calculated by the weight calculating section 67. A post-movement particle position of each particle 72 moved by the particle moving section 65 becomes a likely position (a position at which the sensor unit is placed with a high probability) of the sensor unit $S_i$ in the inserting section 11 configured to be inserted into a body cavity as the calculated weight of each particle 72 increases. Therefore, the sensor position observing section 69 highly accurately observes the position of the sensor unit $S_i$. The sensor position compensating section 55 is configured to compensate the position of each sensor unit $S_i$ to the post-movement sensor position which is a position observed by the sensor position observing section 69 in the last estimation in the sensor position estimating section 61. Therefore, the position of the sensor unit $S_i$ after the positional compensation is the likely position (the position at which the sensor unit is placed with a high probability) of the sensor unit $S_i$ in the inserting section 11 configured to be inserted into a body cavity. Since the form correcting section 50 is configured to correct the detected linear form 71 based on the position of the sensor unit $S_i$ after the positional compensation, it is possible to detect the corrected form 75 with less errors as compared with an actual form of the inserting section 11. As a result, the corrected form 75 of the inserting section 11 can be highly accurately detected.

Further, in the endoscopic form detection device 1, the acceleration sensor $A_i$ is configured to measure gravitational acceleration and the geomagnetic sensor $B_i$ is configured to measure geomagnetism in the stationary state in which the inserting section 11 is not moving. Furthermore, the posture detecting section 30 is configured to detect a posture of each sensor unit $S_i$ from the measured gravitational acceleration and geomagnetism. In the stationary state, each of the gravitational acceleration and the geomagnetism always has a fixed intensity in a fixed direction. Since a posture of each sensor unit $S_i$ is detected from the gravitational acceleration and the geomagnetism, the posture of the sensor unit $S_i$ can be highly accurately detected even in the stationary state. As a result, the corrected form 75 of the inserting section 11 can be highly accurately detected.

Second Embodiment

A second embodiment according to the present invention will now be described with reference to FIG. 16 to FIG. 21. It is to be noted that like reference numerals denote parts equal to those in the first embodiment or parts having functions equal to those in the same, thereby omitting description thereof.

FIG. 16 is a view showing a configuration of a form correcting section 150 according to this embodiment. The form correcting section 150 is configured to compensate a position (a state) of each sensor unit $S_i$ by using a particle filter and to correct a detected linear form 71 detected by a linear form detecting section 40. FIG. 17 is a view showing a corrected form 175 of an inserting section 11 of an endoscope 10 corrected by the form correcting section 150 from a positive direction of a Z axis of a global coordinate C. As shown in FIG. 17, the form correcting section 150 is configured to correct the detected linear form 71 indicated by a dotted line in FIG. 17 to the corrected form 175. When a position of each sensor unit $S_i$ is compensated, a form of each link $T_j$ is corrected to determine an arc (a corrected inter-sensor element) $L_j$. The corrected form 175 is constituted of the respective arcs $L_j$. A form of the inserting section 11 of the endoscope 10 when inserted into a body cavity is actually a curved form. Here, although there are differences among products, the inserting section 11 of the endoscope 10 has appropriate elasticity. Therefore, a curvature of the curved form of the inserting section 11 varies only slightly. Therefore, when the form correction is performed on the assumption that a form between the sensor units $S_i$ is the arc $L_j$ having a predetermined radius (curvature), it is possible to form the corrected form 175 having a small error from an actual curved form of the inserting section 11.

As shown FIG. 16, the form correcting section 150 includes a form correction sequentially implementing section 151, a form correction controlling section 152, and an uncorrected link position compensating section 153. The form correction sequentially implementing section 151 is configured to sequentially perform the form correction in accordance with each link $T_j$ in the order starting from the link $T_j$ on a proximal end side (a side close to an origin of a global coordinate system C), thereby forming the arc (the corrected inter-sensor element) $L_j$. That is, the form correction sequentially implementing section 51 according to the first embodiment forms the corrected link $T'_j$, whereas the form correction sequentially implementing section 151 according to this embodiment forms the arc $L_j$. The form correction controlling section 152 and the uncorrected link position compensating section 153 have the same configurations and functions as the form correction controlling section 52 and the uncorrected link position compensating section 53 according to the first embodiment, thereby omitting description thereof.

The form correction sequentially implementing section 151 includes a sensor position compensating section (a sensor state compensating section) 155 configured to compensate a position of a sensor unit (a state compensation target sensor) $S_j$ on a distal end side (a side far from the origin of the global coordinate system C) of a link (a correction target link) $T_j$ as a correction target, and an arc forming section (a corrected inter-sensor element forming section) 157 configured to form the arc $L_j$ based on the position of the sensor unit $S_j$ corrected by the sensor position correcting section 155. That is, the corrected link forming section 57 according to the first embodiment forms the corrected link $T'_j$ based on a position of the sensor unit $S_j$ after the positional compensation, whereas the arc forming section 157 according to this embodiment forms the arc $L_j$.

The form correction sequentially implementing section 151 includes a sensor position estimating section (a sensor state estimating section) 161 configured to uses the particle filter to estimate a position of the sensor unit $S_j$ on the distal end side of the link $T_j$ as a correction target. The sensor position estimating section 161 is configured to perform the first positional estimation of the sensor unit $S_j$ based on an initial position provided at a distal end of the link $T_j$. Further, the sensor position estimating section 161 is configured to carry out the second positional estimation and observation of the sensor unit $S_j$ based on a result of the first estimation. That is, the sensor position estimating section 161 uses the particle filter to carry out the positional estimation of the sensor unit $S_j$ based on the initial position or a result of the previous estimation. Furthermore, the form correction sequentially implementing section 151 includes a position estimation controlling section (a state estimation controlling section) 162 configured to control the sensor position estimating section 161 to perform the positional estimation of the sensor unit $S_j$ for a predetermined number of times.

The sensor position estimating section 161 includes a particle dispersing section 163, a curve interpolating section 165 as a particle moving section, a weight calculating section 167, and a sensor position observing section (a sensor state observing section) 169. Detail as of the particle dispersing section 163, the curve interpolating section 165, the weight calculating section 167, and the sensor position observing section 169 will be described later.

Here, description will now be given as to a method of using the form correcting section 150 to correct the detected linear form 71 detected by the linear form detecting section 40. As shown in FIG. 4, the form correcting section 150 is configured to compensate a position of each sensor unit $S_i$ by using the particle filter to correct the detected linear form 71 detected by the linear form detecting section 40 (a step S106).

When compensating a position of each sensor unit $S_i$ to correct the detected linear form 71, the form correction sequentially implementing section 151 is configured to sequentially carry out the form correction in accordance with each link $T_j$ in the order starting from the link $T_j$ on the proximal end side (the side close to the origin of the global coordinate system C), thereby forming the arc $L_j$. Here, a method of using the form correction sequentially implementing section 51 to correct a form of the link $T_j$ will now be described. Here, description will be given as to the form correction of a kth link $T_k$ from the proximal end side between a kth sensor unit $S_{k-1}$ from the proximal end side and a (k+1)th sensor unit $S_k$ from the proximal end side.

Figure 18:
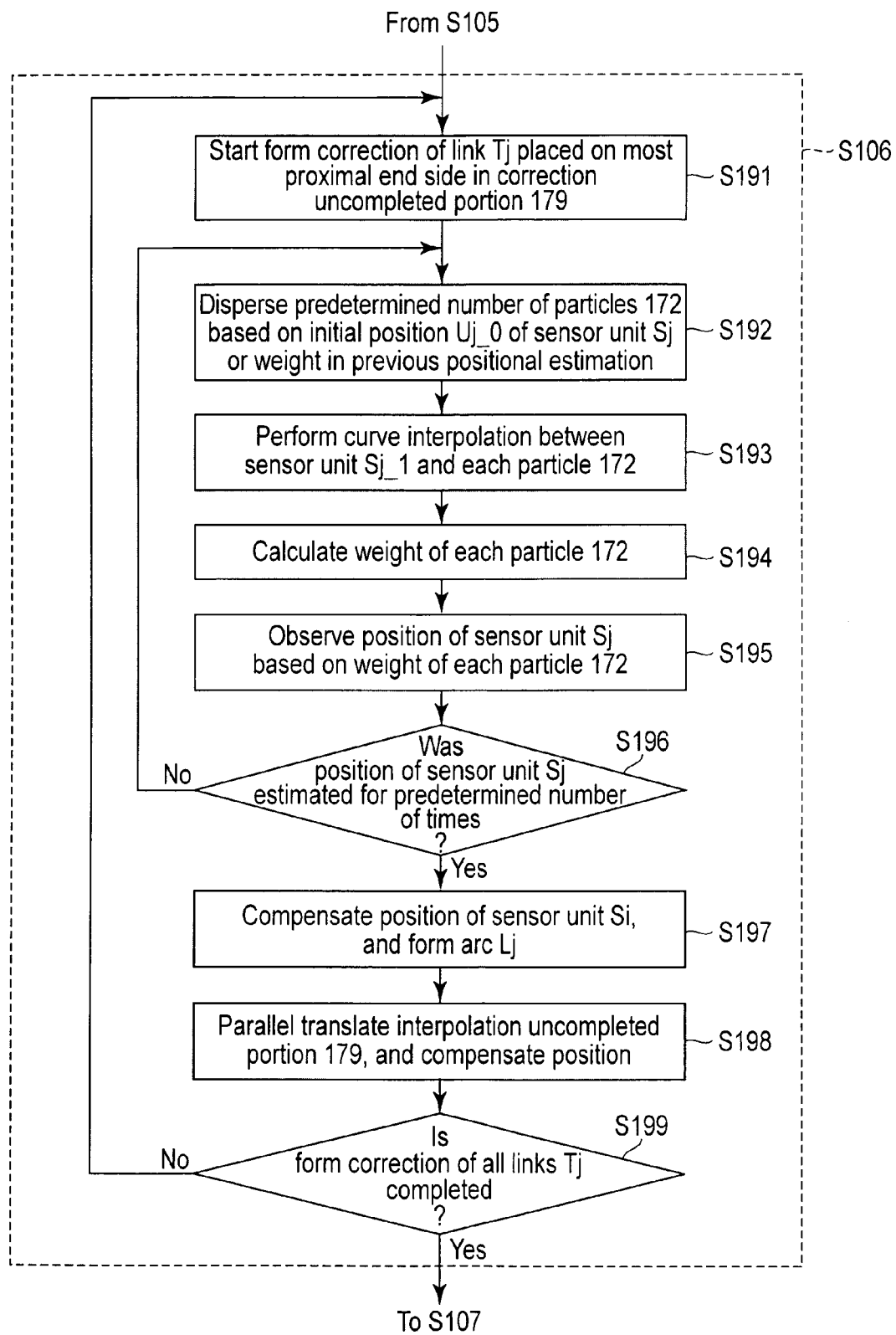
FIG. 18 is a flowchart showing a method of correcting a form of a detected linear form by the form correcting section according to the second embodiment.
Figure 19:
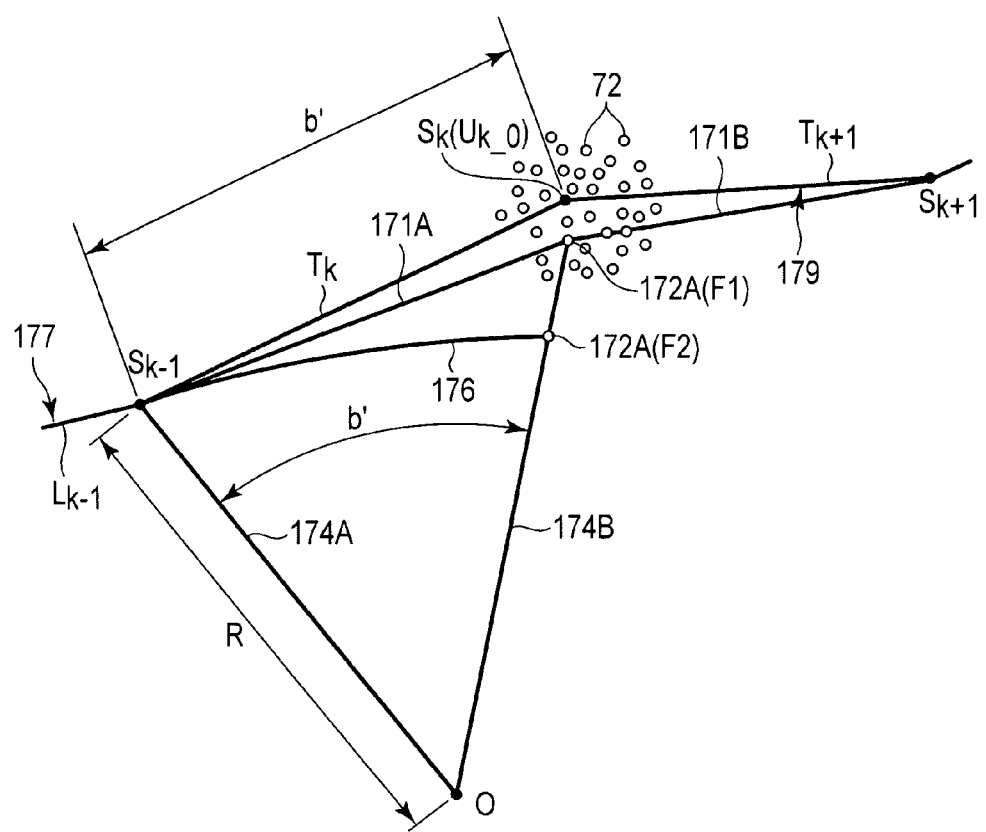
FIG. 19 is a schematic view explaining processing in a particle dispersing section and a curve interpolating section of a sensor position observing section of the form correcting section according to the second embodiment.
Figure 20:
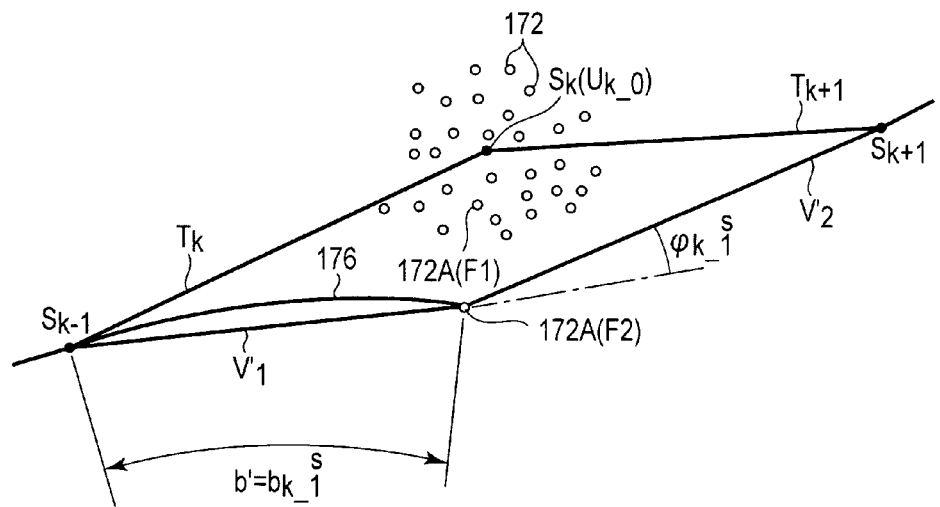
FIG. 20 is a schematic view explaining processing in a weight calculating section of the sensor position observing section of the form correcting section according to the second embodiment.
Figure 21:
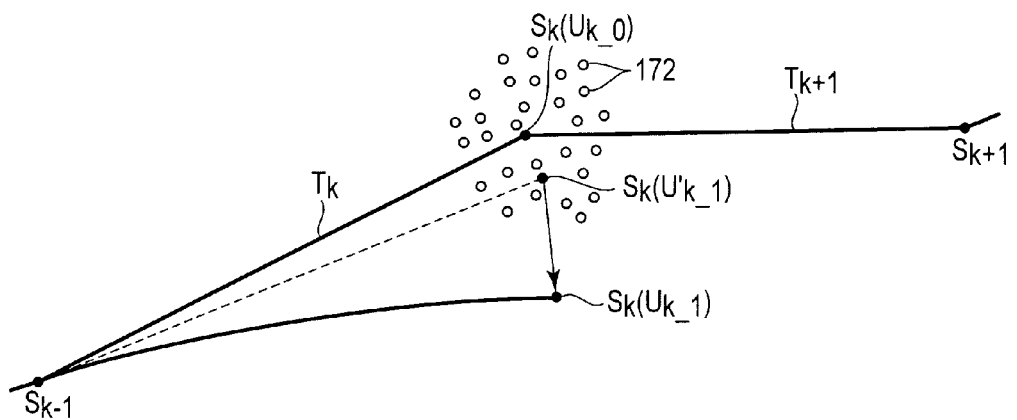
FIG. 21 is a schematic view explaining processing in a sensor position estimating section of the sensor position observing section of the form correcting section according to the second embodiment.

FIG. 18 is a flowchart showing a method of using the form correcting section 150 to correct the form of the detected linear form 71. FIG. 19 to FIG. 21 are views explaining processing in the form correction sequentially implementing section 151. As shown in FIG. 19, in a state before the form correction of the link $T_k$ is carried out by the form correction sequentially implementing section 151, the form correction from the first link to the link $T_{k-1}$ is completed like the first embodiment, thereby forming a correction completed portion 177. Further, a correction uncompleted portion 179 constituted of the links $T_k$ to $T_N$ is also formed. At this time, a boundary between the correction completed portion 177 and the correction uncompleted portion 179 is continuous, and the sensor unit $S_k$ is placed at a point $U_{k\_0}$ in the global coordinate system C.

As shown in FIG. 18 and FIG. 19, in this state, the form correction sequentially implementing section 151 starts the form correction of the link (a correction target link) $T_k$ placed on the most proximal end side in the correction uncompleted portion 179 (a step S191). That is, the form correction controlling section 152 is configured to control the form correction sequentially implementing section 151 to perform the form correction of the link $T_k$.

When performing the form correction of the link $T_k$ by the form correction sequentially implementing section 51, the sensor position estimating section 161 first uses the particle filter to estimate a position of the sensor unit (a state compensation target sensor) $S_k$ on the distal end side of the link $T_k$ based on an initial position ($U_{k\_0}$) placed at the distal end of the link $T_k$. As shown in FIG. 18 and FIG. 19, when estimating the position of the sensor unit $S_k$ based on the initial position, the particle dispersing section 163 first disperses a predetermined number (A in this embodiment) of particles 172 around the initial position $U_{k\_0}$ of the sensor unit $S_k$ on the distal end side of the link $T_k$ (a step S192). Here, the respective particles 172 are uniformly dispersed in the range of Expression (17) like the first embodiment.

Furthermore, the curve interpolating section 165 is configured to perform curve interpolation between a sensor unit $S_{k-1}$ and each particle 172 dispersed by the particle dispersing section 163 (a step S193). The curve interpolating section 165 is configured to perform the curve interpolation by using a transfer model based on a bent state of the inserting section 11, thereby moving a position of each particle 172. That is, the curve interpolating section 165 is a particle moving section configured to use the transfer model based on the bent state of the inserting section 11 to move each particle 172. Each particle 172 is moved from a pre-interpolation particle position (a pre-movement particle position) to a post-interpolation particle position (a post-movement particle position) by the curve interpolating section 165.

Here, description will be given as to the curve interpolation between the sensor unit $S_{k-1}$ and a particle 172A as one of the particles 172. As shown in FIG. 19, in a state before performing the curve interpolation of a curve interpolation link $T_k$ between the sensor unit $S_{k-1}$ and the particle 172A, the particle 172A is placed at a pre-interpolation particle position F1. Here, a line segment connecting the sensor unit $S_{k-1}$ to the pre-interpolation particle position F1 of the particle 172A is determined as a first linear form 171A. A dimension of the first linear form 171A is b'. Moreover, a line segment connecting the pre-interpolation particle position F1 of the particle 172A to a sensor unit $S_{k+1}$ placed at a distal end of the link $T_k$ is determined as a second linear form 171B. Additionally, a first interpolation normal line 174A that runs through a proximal end of the first linear form 171A and is perpendicular to the first linear form 171A and a second interpolation normal line 174B that runs through a distal end of the first linear form 171A and is perpendicular to the second linear form 171B are formed. Further, an intersection O of the first interpolation normal line 174A and the second interpolation normal line 174B is calculated. If the first interpolation normal line 174A and the second interpolation normal line 174B do not cross each other, an intermediate point O of two points that minimize a distance between the first interpolation normal line 174A and the second interpolation normal line 174B is calculated. Furthermore, an arc 176 is formed with the intersection O or the intermediate point O being at the center O. The arc 176 has a radius R equal to a distance between the center O and the proximal end of the first linear form 171A. That is, the arc 176 has a curvature 1/R. Moreover, the arc 176 is the arc 176 that a length of an arc having a starting point at the proximal end of the first linear form 171A is equal to the dimension b' of the first linear form 171A. A distal end F2 of the arc 176 is the post-interpolation particle position F2 of the particle 172A. That is, a position of the particle 172A is moved from the pre-interpolation particle position F1 to the post-interpolation particle position F2 based on the curve interpolation carried out by the curve interpolating section 165. Each of the other particles is likewise moved from the pre-interpolation particle position to the post-interpolation particle position.

Further, like the first embodiment, the weight calculating section 167 is configured to calculate a weight $w_{k\_1}^a$ of each particle 172 (a step S194). That is, the weight of each particle 172 is updated from the initial value $w_{k\_0}^a$ to $w_{k\_1}^a$. The weight calculating section 167 first calculates likelihood $v_{k\_1}^a$ for evaluating how likely the post-interpolation particle position (the post-movement particle position) of each particle 172 is. The likelihood is calculated by using Expression (18) to Expression (20). However, in this embodiment, $b_{k\_1}^a$ is an arc length of an arc between the sensor unit $S_{k-1}$ after the positional compensation and the post-interpolation particle position of each particle 172. For example, as shown in FIG. 20, the arc length b' of the arc 176 formed between the sensor unit $S_{k-1}$ and the particle 172A (a=s in this particle) as described above is $b_{k-1}^s$. Moreover, in Expression (19), $b_0$ is determined as an inter-sensor dimension l of each sensor unit $S_i$. Based on Expression (19), a function $h(b_{k\_1}^a)$ increases and the likelihood becomes large as a difference between inter-sensor dimension l and an arc length of the arc between the sensor unit $S_{k-1}$ after the positional compensation and the particle 172 decreases. Contrarily, the function $h(b_{k\_1}^a)$ decreases and the likelihood becomes small as the difference between the inter-sensor dimension l and the arc length of the arc between the sensor unit $S_{k-1}$ after the positional compensation and the particle 172 increases. However, since the arc length of the arc between the sensor unit $S_{k-1}$ after the positional compensation and the post-interpolation particle position of each particle 172 is equal to the dimension of the line segment between the sensor unit $S_{k-1}$ after the positional compensation and the pre-interpolation particle position of each particle 172, the same result can be obtained when $b_{k-1}^a$ is the dimension of the line segment between the sensor unit $S_{k-1}$ and the pre-interpolation particle position of each particle 172. Additionally, in this embodiment, $\phi_{k\_1}^a$ is an angle formed between a vector V'1 from the sensor unit $S_{k-1}$ after the positional compensation to the post-interpolation particle position of each particle 172 and a vector V'2 from the post-interpolation particle position of each particle 172 to the sensor unit $S_{k+1}$ before the positional compensation. For example, as shown in FIG. 20, in the case of the particle 172A (a=s in this particle), an angle formed between the vector V'1 from the sensor unit $S_{k-1}$ to the post-interpolation particle position F2 of the particle 172A and the vector V'2 from the post-interpolation particle position F2 of the particle 172A to the sensor unit $S_{k+1}$ is $\phi_{k\_1}{}^s$. Based on Expression (20), if the angle formed between the vectors V'1 and V'2 falls within the range of 0 degrees to ±90 degrees, the function $g(\phi_{k\_1}{}^a)$ increases and the likelihood becomes large. Contrarily, in the case of any other angle, the function $g(\phi_{k\_1}{}^a)$ decreases, and the likelihood becomes small. Further, the weight $w_{k\_1}{}^a$ is calculated from the likelihood of each particle 172 by using Expression (21).

Furthermore, the sensor position observing section 169 is configured to observe a position of the sensor unit $S_k$ based on the weight of each particle 172 calculated by the weight calculating section 67 (a step S195). At this moment, as shown in FIG. 21, the sensor position observing section 169 calculates a weighted mean of the pre-interpolation particle positions of the respective particles 172 before interpolated by the curve interpolating section 165, and it determines the calculated position as a pre-interpolation sensor position $U'_{k\_1}$. Moreover, based on the transfer model used by the particle moving section 65 when performing the curve interpolation, movement from the pre-interpolation sensor position $U'_{k\_1}$ to a post-interpolation sensor position $U_{k\_1}$ is carried out, and the post-interpolation sensor position $U_{k\_1}$ is estimated as a position of the sensor unit $S_k$.

Additionally, the position estimation controlling section 162 is configured to judge whether estimation of the position of the sensor unit $S_k$ has been carried out for a predetermined number of times (M times in this embodiment) (a step S196). Under existing circumstances, since the estimation of the position of the sensor unit $S_k$ has been performed only once (the step S196—No), the sensor position estimating section 161 is controlled to a state in which the estimation of the position of the sensor unit $S_k$ is carried out one more time by the position estimation controlling section 162. In the second or subsequent estimation of the position, the sensor position estimating section 161 is configured to estimate the position of the sensor unit $S_k$ based on an estimation result of the previous estimation of the position.

Moreover, the processing returns to the step S192 where the particle dispersing section 163 disperses the predetermined number (A in this embodiment) of the particles 72 (the step S192). In the second or subsequent estimation of the position, the particle dispersing section 163 is configured to disperse the particles 172 based on the weight of each particle 172 calculated by the weight calculating section 167 at the time of the previous positional estimation. As a result, for example, the number of the particles 172 to be dispersed is increased around the pre-interpolation particle positions of the particles 172 having large weights calculated in the previous positional estimation. On the other hand, the number of the particles 172 is reduced around the pre-interpolation particle positions of the particles 172 having small weights calculated in the previous positional estimation.

Further, in the second or subsequent positional estimation, likewise, the curve interpolating section 165 is configured to carry out the curve interpolation between the sensor unit $S_{k-1}$ and each particle 172 based on the transfer model used in the first estimation (a step S193). As a result, each particle 172 moves from the pre-interpolation particle position to the post-interpolation particle position.

Furthermore, the weight calculating section 167 uses the same expressions as Expression (18) to Expression (20) to calculate the likelihood for evaluating how likely it is that the sensor unit $S_k$ is placed at the post-interpolation particle position of each particle 172. Based on the likelihood, the plausibility of the post-interpolation particle position of each particle 172 is detected. Moreover, the weight of each particle 72 is calculated from the likelihood by using the same expression as Expression (21) (a step S194). Here, for example, in t-th positional estimation, likelihood $v_{k\_t}{}^a$ and weights $w_{k\_t}{}^a$, $b_{k\_t}{}^a$, and $\phi_{k\_t}{}^a$ are used for calculation in place of the likelihood $v_{k\_1}{}^a$ and weights $w_{k\_1}{}^a$, $b_{k\_1}{}^a$, and $\phi_{k\_1}{}^a$ in Expression (18) to Expression (21).

Moreover, the sensor position observing section 169 is configured to observe the position of the sensor unit $S_k$ based on the weight of each particle 172 calculated by the weight calculating section 167 (a step S195). For example, in the t-th positional estimation, the pre-interpolation sensor position $U'_{k\_t}$ is calculated from the weighted mean of the respective particles 172, and the curve interpolation is performed by using the above-described transfer model. Based on the curve interpolation, the movement from the pre-interpolation sensor position $U'_{k\_t}$ to the post-interpolation sensor position $U_{k\_t}$ is effected.

Further, the positional estimation controlling section 162 is configured to judge whether the position of the sensor unit $S_k$ has been estimated for a predetermined number of times (M in this embodiment) (a step S196). When the position of the sensor unit $S_k$ has not been estimated for the predetermined number of times (the step S196—No), the position estimation controlling section 162 controls the sensor position estimating section 161 to estimate the position of the sensor unit $S_k$ one more time, and the step S192 to the step S195 are performed one more time. When the position of the sensor unit $S_k$ has been estimated for the predetermined number of time (the step S196—Yes), the processing advances to the next step.

As shown in FIG. 17, after estimating the position of the sensor unit $S_k$ for the predetermined number of times (e.g., twice), the sensor position compensating section 155 is configured to compensate the position of the sensor unit (a state compensation target sensor) $S_k$ on the distal end side of the link as a correction target (a correction target link) $T_k$ based on an estimation result of the sensor position estimating section 161 (a step S197). The sensor position compensating section 155 is configured to compensate the position of the sensor unit $S_k$ from the initial position ($U_{k\_0}$) provided at the distal end of the link $T_k$ to a post-interpolation sensor position $U_{k\_M}$ of the sensor unit $S_k$ estimated in the last (the mth in this embodiment) positional estimation performed by the sensor position observing section 61. Furthermore, the arc forming section 157 is configured to form an arc $L_k$ based on the position of the sensor unit $S_k$ compensated by the sensor position compensating section 155 (a step S197). Here, an arc connecting the sensor unit $S_{k-1}$ subjected to the positional compensation and the post-movement sensor position $U_{k\_M}$ of the sensor unit $S_k$ is the arc $L_k$. It is to be noted that the arc connecting the sensor unit $S_{k-1}$ subjected to the positional compensation and the post-interpolation sensor position $U_{k\_M}$ of the sensor unit $S_k$ is formed by performing the curve interpolation between the sensor unit $S_{k-1}$ and the pre-interpolation sensor position $U'_{k\_M}$ of the sensor unit $S_k$ with the use of above-mentioned transfer model. Based on the movement of the position of the sensor unit $S_k$, a boundary between the correction completed portion 177 and the correction uncompleted portion 179, which is continuous before the form correction of the link $T_k$ is carried out by the form correction sequentially implementing section 151, becomes discontinuous. That is, the arc $L_k$ and the link $T_{k+1}$ are discontinuous.

Further, like the first embodiment, in this state, the uncorrected link position compensating section 153 is configured to parallel translate the correction uncompleted portion 179 in such a manner that the boundary between the correction uncompleted portion 179 and the correction completed portion 177 becomes continuous, thereby compensating the position of the correction uncompleted portion 179 (a step S198).

It is to be noted that, in regard to each link $T_j$ other than the link $T_k$, the form correction sequentially implementing section 151 likewise is configured to perform the form correction, thereby forming the arc $L_j$. Furthermore, the uncorrected link position compensating section 53 is configured to compensate the position of the correction uncompleted portion 179 every time a form of one link $T_j$ is corrected by the form correction sequentially implementing section 151.

Furthermore, as shown in FIG. 17, the form correction controlling section 152 is configured to confirm whether the form correction of all the links $T_j$ has been completed (a step S199). If the form correction of all the links $T_j$ has been completed, the corrected form 175 of the inserting section 11 is formed, and the processing advances to the next step (the step S199—Yes). If the form correction of all the links $T_j$ has not been completed, the processing returns to the step S191 (the step S199—No), and the form correction sequentially implementing section 151 corrects a form of a link (a correction target link) $T_j$ placed on the most proximal side (the side close to the origin of the global coordinate system C) in the correction uncompleted portion 179. That is, the steps S191 to S198 are repeated until the form correction of all the links $T_j$ is completed.

Therefore, the endoscopic form detection device 1 and the form detection method of the inserting section 11 of the endoscope 10 using the endoscopic form detection device 1 exercise the following effects.

That is, in the endoscopic form detection device 1, the posture detecting section 30 is configured to detect a posture of each sensor unit $S_i$ from measurement data of each sensor unit $S_i$, and the linear form detecting section 40 is configured to detect the detected linear form 71 of the inserting section 11 of the endoscope 10 from the posture of each sensor unit $S_i$. Further, the form correcting section 50 is configured to compensate a position of each sensor unit $S_i$ by using the particle filter and to correct the detected linear form 71 detected by the linear form detecting section 40. Furthermore, the corrected form 175 of the inserting section 11 is formed. As described above, since the corrected form 175 of the inserting section 11 is detected from the measurement data of each sensor unit $S_i$ arranged in the inserting section 11 configured to be inserted into a body cavity at the time of observation, a sense coil and others do not have to be provided outside a body. Therefore, miniaturization and simplification of the endoscopic form detection device 1 can be realized.

Moreover, in the endoscopic form detection device 1, the form correcting section 150 is configured to compensate a position of each sensor unit $S_i$ by using the particle filter and to correct the detected linear form 71. In the form correcting section 150, the sensor position estimating section 161 of the form correction sequentially implementing section 151 is configured to estimate each sensor unit $S_i$ for a predetermined number of times. When estimating each sensor unit $S_i$, the weight calculating section 167 is configured to calculate a weight of each particle 72. Additionally, the sensor position observing section 169 is configured to observe the position of each sensor unit $S_i$ based on the weight of each particle 172 calculated by the weight calculating section 167. A post-interpolation particle position (a post-movement particle position) of each particle 172 interpolated based on the curve interpolation in the curve interpolating section 165 becomes a likely position (a position at which the sensor unit is placed with a high probability) of the sensor unit $S_i$ in the inserting section 11 configured to be inserted into a body cavity as the calculated weight of each particle 72 increases. Therefore, the sensor position observing section 169 highly accurately observes the position of the sensor unit $S_i$. The sensor position compensating section 155 is configured to compensate the position of each sensor unit $S_i$ to the post-interpolation sensor position (the post-movement sensor position) which is a position observed by the sensor position observing section 169 in the last estimation in the sensor position estimating section 161. Therefore, the position of the sensor unit $S_i$ after the positional compensation is the likely position (the position at which the sensor unit is placed with a high probability) of the sensor unit $S_i$ in the inserting section 11 configured to be inserted into a body cavity. Since the form correcting section 150 corrects the detected linear form 71 based on the position of the sensor unit $S_i$ after the positional compensation, it is possible to detect the corrected form with less errors as compared with an actual form of the inserting section 11. As a result, the corrected form 75 of the inserting section 11 can be highly accurately detected.

Additionally, in the endoscopic form detection device 1, the form correction sequentially implementing section 151 is configured to correct the form of each link $T_j$ into the arc (the corrected inter-sensor element) $L_j$. The actual form of the inserting section 11 of the endoscope 10 when inserted into a body cavity is a curved form. Although there are differences among products, the inserting section 11 of the endoscope 10 has appropriate elasticity. Therefore, a curvature of the curved form of the inserting section 11 varies only slightly. Therefore, when a form between the sensor units $S_i$ is corrected into the arc $L_j$ having a predetermined radius (curvature), it is possible to detect the corrected form 175 having a small error from an actual curved form of the inserting section 11.

Modification of First Embodiment

A modification of the first embodiment will now be described. It is to be noted that like reference numerals denote the same parts or parts having the same functions as those in the first embodiment, thereby omitting description thereof.

In this modification, it is possible to detect a corrected form 75 of an inserting section 11 in a moving state in which the inserting section 11 of an endoscope 10 is being parallel translated. That is, a particle moving section 65 of a sensor position estimating section 61 is configured to move each particle 72 based on acceleration data in the moving state measured by an accelerator sensor $A_i$ of each sensor unit $S_i$.

When moving each particle based on the acceleration data in the moving state, an acceleration detecting section (not shown) provided in a personal computer 8 first acquires the acceleration data in the moving state measured by the acceleration sensor $A_i$ of each sensor unit $S_i$.

Further, the acceleration detecting section is configured to divide an acceleration vector measured at the center of each sensor unit $S_i$ into an X axis directions component, a Y axis directions component, and a Z axis directions component in a global coordinate system C based on the acceleration data in the moving state. Furthermore, the X axis directions component, the Y axis directions component, and the Z axis directions component in the global coordinate system C of the acceleration vector measured at the center of each sensor unit $S_i$ are detected. In the moving state, since a component based on movement of the inserting section 11 is added to gravitation acceleration generated in the vertical directions in a stationary state, the X axis directions component, the Y axis directions component, and the Z axis directions component in the global coordinate system C of the acceleration vector measured at the center of each sensor unit $S_i$ are determined as follows:

$$\dot{a}_{thi} = [a_{thi\_X} \ a_{thi\_Y} - g + a_{thi\_Z}]^T \quad (22)$$

Moreover, an $X_i$ axis directions component, a $Y_i$ axis directions component, and a $Z_i$ axis directions component in a local coordinate system $C_i$ of an acceleration vector measured by the acceleration sensor $A_i$ of each sensor unit $S_i$ are determined as follows:

$$\dot{a}_{obsi}' = [a_{Bi\_X}' a_{Bi\_Y}' a_{Bi\_Z}']^T \tag{23}$$

Additionally, in this modification, since a situation where the inserting section 11 of the endoscope 10 is parallel translated is considered, it is assumed that the acceleration vector in the global coordinate system C is the same in the sensor units $S_i$ arranged in proximity with respect to each other. In the actual endoscope 10, since an inter-sensor dimension l between the respective sensor units $S_i$ is very small, such assumption is possible. When such assumption is made, for example, the following expressions can be achieved between an acceleration vector measured in a sensor unit $S_1$ and an acceleration vector measured in a sensor unit $S_2$:

$$\dot{a}_{th1} = \dot{a}_{th2} \tag{24.1}$$

$$\|\dot{a}_{obs1}'\| = \|\dot{a}_{obs2}'\| \tag{24.2}$$

Additionally, based on Expression (24.1) and Expression (24.2), the following relationships can be achieved:

$$[a_{th1\_X} a_{th1\_Y} a_{th1\_Z}]^T = [a_{th2\_X} a_{th2\_Y} a_{th2\_Z}]^T \tag{25.1}$$

$$[a_{B1\_X}' a_{B1\_Y}' a_{B1\_Z}']^T = [a_{B2\_X}' a_{B2\_Y}' \sqrt{\|a_{obs1}'\|^2 - (a_{B2\_X}'^2 + a_{B2\_Y}'^2)}]^T \tag{25.2}$$

Here, in the sensor unit $S_1$, based on a relationship between the global coordinate system C and the local coordinate system $C_1$, a rotation matrix in Expression (1) is used to achieve the following expression:

$$\dot{a}_{obs1}' = (C_{B1}^G)^T \dot{a}_{th1} \tag{26}$$

$$= \begin{bmatrix} -\sin\gamma_1 \cdot \sin\alpha_1 \cdot \sin\beta_1 + \cos\beta_1 \cdot \cos\gamma_1 & -\sin\gamma_1 \cdot \cos\alpha_1 & \sin\gamma_1 \cdot \sin\alpha_1 \cdot \cos\beta_1 + \sin\beta_1 \cdot \cos\gamma_1 \\ \cos\gamma_1 \cdot \sin\alpha_1 \cdot \sin\beta_1 + \cos\beta_1 \cdot \sin\gamma_1 & \cos\gamma_1 \cdot \cos\alpha_1 & -\cos\gamma_1 \cdot \sin\alpha_1 \cdot \cos\beta_1 + \sin\beta_1 \cdot \sin\gamma_1 \\ -\cos\alpha_1 \cdot \sin\beta_1 & \sin\alpha_1 & \cos\alpha_1 \cdot \cos\beta_1 \end{bmatrix}$$

$$\begin{bmatrix} a_{th1\_X} \\ a_{th1\_Y} \\ -g + a_{th1\_Z} \end{bmatrix}$$

Likewise, in the sensor unit $S_2$, based on a relationship between the global coordinate system C and a local coordinate system $C_2$, the rotation matrix in Expression (1) is used to attain the following expression:

$$\dot{a}_{obs2}' = (C_{B2}^G)^T \dot{a}_{th2} \tag{27}$$

$$= \begin{bmatrix} -\sin\gamma_2 \cdot \sin\alpha_2 \cdot \sin\beta_2 + \cos\beta_2 \cdot \cos\gamma_2 & -\sin\gamma_2 \cdot \cos\alpha_2 & \sin\gamma_2 \cdot \sin\alpha_2 \cdot \cos\beta_2 + \sin\beta_2 \cdot \cos\gamma_2 \\ \cos\gamma_2 \cdot \sin\alpha_2 \cdot \sin\beta_2 + \cos\beta_2 \cdot \sin\gamma_2 & \cos\gamma_2 \cdot \cos\alpha_2 & -\cos\gamma_2 \cdot \sin\alpha_2 \cdot \cos\beta_2 + \sin\beta_2 \cdot \sin\gamma_2 \\ -\cos\alpha_2 \cdot \sin\beta_2 & \sin\alpha_2 & \cos\alpha_2 \cdot \cos\beta_2 \end{bmatrix}$$

$$\begin{bmatrix} a_{th2\_X} \\ a_{th2\_Y} \\ -g + a_{th2\_Z} \end{bmatrix}$$

When the relationship represented by Expression (25.1) is utilized to solve Expressions (26) and (27), it is possible to obtain an X axis directions component $a_{th1\_X}(a_{th2\_X})$, a Y axis directions component $a_{th1\_Y}(a_{th2\_Y})$, and a Z axis directions component $a_{th1\_Z}(a_{th2\_Z})$ in the global coordinate system C of an acceleration vector other than the gravitational acceleration measured by each of the sensor unit $S_1$ and $S_2$. A relationship between respective axis directions components in the global coordinate system C of a geomagnetic vector measured by a geomagnetic sensor $B_i$ represented by Expression (13) and respective axis directions components in the local coordinate system $C_i$ of a geomagnetic vector represented by Expression (9) is as follows by using the rotation matrix in Expression (1):

$$\dot{M}_{obsi} = (C_{Bi}^G)^T \dot{M}_{th} \tag{28}$$

$$= \begin{bmatrix} -\sin\gamma_i \cdot \sin\alpha_i \cdot \sin\beta_i + \cos\beta_i \cdot \cos\gamma_i & -\sin\gamma_i \cdot \cos\alpha_i & \sin\gamma_i \cdot \sin\alpha_i \cdot \cos\beta_i + \sin\beta_i \cdot \cos\gamma_i \\ \cos\gamma_i \cdot \sin\alpha_i \cdot \sin\beta_i + \cos\beta_i \cdot \sin\gamma_i & \cos\gamma_i \cdot \cos\alpha_i & -\cos\gamma_i \cdot \sin\alpha_i \cdot \cos\beta_i + \sin\beta_i \cdot \sin\gamma_i \\ -\cos\alpha_i \cdot \sin\beta_i & \sin\alpha_i & \cos\alpha_i \cdot \cos\beta_i \end{bmatrix}$$

$$\begin{bmatrix} E_X \\ E_Y \\ E_Z \end{bmatrix}$$

When solving Expressions (25.1), (26), and (27) including a relational expression of geomagnetism obtained by assigning i=1 (or 2) in Expression (28), there are six unknown posture angles and six unknown acceleration values, and hence a total of 12 unknowns are present with respect to 12 equations. As a result, it is possible to mathematically solve the X axis directions component $a_{th1\_X}(a_{th2\_X})$, the Y axis directions component $a_{th1\_Y}(a_{th2\_Y})$, and the Z axis directions component $a_{th1\_Z}(a_{th2\_Z})$ in the global coordinate system C of the acceleration vector other than the gravitational acceleration measured by each of the sensor unit $S_1$ and $S_2$. In regard to any other sensor unit $S_i$, likewise, an X axis directions component $a_{thi\_X}$, a Y axis directions component $a_{thi\_Y}$, and a Z axis directions component $a_{thi\_Z}$ in the global coordinate system C of an acceleration vector other than the gravitational acceleration measured by each sensor unit $S_i$ can be obtained.

Moreover, a displacement calculating section (not shown) provided in the personal computer 8 is configured to calculate a displacement of each sensor unit $S_i$ from the previous stationary state based on the acceleration vector other than the gravitational acceleration detected by the acceleration detecting section. An X axis directions component, a Y axis directions component, and a Z axis directions component in the global coordinate system C of the displacement of each sensor unit $S_i$ from the previous stationary state can be obtained by performing double integration with respect to the X axis directions component $a_{thi\_X}$, the Y axis directions component $a_{thi\_Y}$, and the Z axis directions component $a_{thi\_Z}$ in the global coordinate system C of an acceleration vector other than the gravitational acceleration measured by each sensor unit $S_i$. Additionally, the displacement calculating section also is configured to calculate an X axis directions component, a Y axis directions component, and a Z axis directions component in the global coordinate system C of a velocity vector of each sensor unit $S_i$. The X axis directions component, the Y axis directions component, and the Z axis directions component in the global coordinate system C of the velocity vector of each sensor unit $S_i$ can be obtained by performing integration only once with respect to the X axis directions component $a_{thi\_X}$, the Y axis directions component $a_{thi\_Y}$, and the Z axis directions component $a_{thi\_Z}$ in the global coordinate system C of the acceleration vector other than the gravitational acceleration measured by each sensor unit $S_i$.

A particle moving section 65 is configured to detect a transfer model of each particle 72 based on X axis directions components, Y axis directions components, and Z axis directions components in the global coordinate system C of an acceleration vector, a velocity vector, and displacement of each sensor unit $S_i$ detected by the acceleration detecting section and the displacement calculating section. Moreover, each particle 72 is moved from a pre-movement particle position to a post-movement particle position based on the transfer model (a step S113 in FIG. 9). That is, the particle moving section 65 serves as a moving-state transfer model implementing section configured to detect the transfer model from the acceleration vector, the velocity vector, and the displacement of each sensor unit $S_i$ detected in the moving state and to move each particle 72 based on the transfer model.

Further, as described above, a weight is calculated from the likelihood of each particle 72 which represents how likely the post-movement particle position is (the step S114). Furthermore, the position of the sensor unit $S_i$ is observed based on the weight of each particle 72 (the step S115). The above-described positional estimation of the sensor unit $S_i$ is performed for a predetermined number of times, and the position of the sensor unit $S_i$ is compensated to the post-movement sensor position estimated in the last positional estimation (the step S117). Moreover, based on the position of the sensor unit $S_j$ after the positional compensation, a corrected inter-sensor element which is a form between the respective sensor units $S_i$ after the form correction is formed (the step S117). As described above, even in the moving state, a corrected form 75 obtained by correcting a detected linear form 71 can be detected.

(Any Other Modification)

It is to be noted that the sensor position compensating section 55 or 155 compensates a position of the sensor unit $S_j$ on the distal end side of the correction target link $T_j$ in the foregoing embodiments, and a posture of the sensor unit $S_j$ may be compensated in addition to performing the positional compensation, for example. That is, the sensor position compensating section 55 or 155 can be a sensor state compensating section configured to compensate at least a position of the sensor unit $S_j$ on the distal end side of the correction target link $T_j$. In this case, the sensor position estimating section 61 or 161 is configured to estimate a posture of the sensor unit $S_j$ by using a particle filter. That is, the sensor position estimating section 61 or 161 is a sensor state estimating section configured to estimate at least a position of the sensor unit $S_j$ by using the particle filter. Furthermore, the sensor position observing section 69 or 169 functions as a sensor state observing section configured to observe at least a position of the sensor unit $S_j$. For example, when estimating a posture of the sensor unit $S_k$, each particle 72 dispersed by the particle dispersing section 63 has a posture in addition to a position in the global coordinate system represented by Expression (17.1) to Expression (17.3). Here, posture angles $\alpha_k$, $\beta_k$, and $\gamma_k$ in a local coordinate system $C_k$ of the sensor unit $S_k$ obtained based on Expression (7), Expression (8), and Expression (12) (or Expression (15)) correspond to an initial posture (an initial state) of the sensor unit $S_k$, and variance of errors of the respective posture angles is represented as $\delta_\alpha$, $\delta_\beta$, and $\delta_\gamma$. In the first estimation, the particles 72 are uniformly dispersed in the range obtained by adding the respective values of variance $\delta_\alpha$, $\delta_\beta$, and $\delta_\gamma$ of errors to the initial posture (the posture angles $\alpha_k$, $\beta_k$, and $\gamma_k$) of the sensor unit $S_k$ acquired by Expression (7), Expression (8), and Expression (12) (or Expression (15)). That is, assuming that posture angles of each particle 72 in the first estimation of the sensor unit $S_k$ are $\alpha_{k\_1}^a$, $\beta_{k\_1}^a$, and $\gamma_{k\_1}^a$ (a=1, 2, . . . , A), the respective particles 72 are uniformly dispersed in the following ranges:

$$\alpha_k - \delta_\alpha \leq \alpha_{k\_1}^a \leq \alpha_k + \delta_\alpha \qquad (29.1)$$

$$\beta_k - \delta_\beta \leq \beta_{k\_1}^a \leq \beta_k + \delta_\beta \qquad (29.2)$$

$$\gamma_k - \delta_\gamma \leq \gamma_{k\_1}^a \leq \gamma_k + \delta_\gamma \qquad (29.3)$$

The respective values of variance $\delta_\alpha$, $\delta_\beta$, and $\delta_\gamma$ of errors are obtained by using Expression (1) to Expression (15) from variance of respective errors in measurement data of the sensor unit $S_i$ generated due to noise and the like. In the second or subsequent estimation, a posture of each particle 72 is determined based on the weight of the particle 72 in the previous estimation.

Moreover, in the foregoing embodiments, each local coordinate system $C_i$ is a coordinate system in which the $Y_i$ axis directions coincide with the longitudinal directions at the center of the sensor unit $S_i$. However, in the present invention, each local coordinate system $C_i$ can be a coordinate system in which an origin is set at the center of the sensor unit $S_i$ and any one of an $X_i$ axis, a $Y_i$ axis, and a $Z_i$ axis is a longitudinal axis whose axial directions coincide with the longitudinal directions at the center of the sensor unit $S_i$. However, when the $X_i$ axis is the longitudinal axis, the following representation is used in place of $e_{yk-1}$ in Expression (16.1) and Expression (16.2):

$$e_{xk-1} = [100]^T \quad (30)$$

Likewise, when the $Z_i$ axis is the longitudinal axis, the following representation is used in place of $e_{yk-1}$ in Expression (16.1) and Expression (16.2):

$$e_{zk-1} = [001]^T \quad (31)$$

where $e_{xk-1}$ is a unit vector in $X_{k-1}$ axis directions which are the longitudinal directions at an origin of a local coordinate system $C_{k-1}$, and $e_{zk-1}$ is a unit vector in $Z_{k-1}$ axis directions which is the longitudinal directions at the origin of the local coordinate system $C_{k-1}$.

Additionally, in the foregoing embodiments, the global coordinate system C is a coordinate system in which an origin is set at the center of a sensor unit $S_0$ on the most proximal end side, a Z axis coincides with the vertical directions, and an X axis and a Y axis are arranged on the horizontal plane. However, in the present invention, it is possible to adopt a coordinate system in which any one of an X axis, a Y axis, and a Z axis is a vertical axis whose axial directions coincide with the vertical directions and two axes other than the vertical axis are horizontal axes which are arranged on the horizontal plane. As a result, the posture detecting section 30 can detect a posture of each sensor unit $S_i$ based on gravitational acceleration measured by the acceleration sensor $A_i$ and geomagnetism measured by the geomagnetic sensor $B_i$. However, when the X axis is the vertical axis, an X axis component, a Y axis component, and a Z axis component in the global coordinate system C of a gravitational acceleration vector represented by Expression (2) are as follows:

$$\dot{a}_{th} = [-g00]^T \quad (32)$$

Further, the geomagnetism does not function in the X axis directions of the global coordinate system C. In this case, although the posture angles $\alpha_i$, $\beta_i$, and $\gamma_i$ are of the (Z, X, Y) type that rotates in the order of the yaw angle $\gamma_i$, the pitch angle $\alpha_i$, and the roll angle $\beta_i$ in the first embodiment, the rotation order of the posture angles $\alpha_i$, $\beta_i$, and $\gamma_i$ is changed, and a rotation matrix different from the rotation matrix in Expression (1) is used. As a result, the posture angles $\beta_i$ and $\gamma_i$ about the Y axis and the Z axis which are horizontal axes can be calculated by the first angle calculating section 34 based on acceleration data measured by the acceleration sensor $A_i$. Furthermore, the posture angle $\alpha_i$ about the X axis which is a vertical axis can be calculated by the second angle calculating section 36 based on geomagnetic data measured by the geomagnetic sensor $B_i$. This operation is likewise performed when the Y axis is the vertical axis, and the posture angles $\alpha_i$ and $\gamma_i$ about the X axis and the Z axis which are the horizontal axes are calculated by the first angle calculating section 34 based on the acceleration data measured by the acceleration sensor $A_i$. Furthermore, the posture angle $\beta_i$ about the Y axis which is the vertical axis is calculated by the second angle calculating section 36 based on the geomagnetic data measured by the geomagnetic sensor $B_i$.

Moreover, although the origin of the global coordinate system C is set at the center of the sensor unit $S_0$ on the most proximal end side in the foregoing embodiment, the origin may be set at the center of the sensor unit $S_N$ on the most distal end side. In this case, the link forming section 41 uses Expression (16.1) and Expression (16.2) to obtain a coordinate $P'_j$ ($l_{xj}$, $l_{yj}$, $l_{zj}$) of the sensor unit $S_{j-1}$ on the proximal end side (the side far from the origin of the global coordinate system C) of the link $T_j$ when the sensor unit $S_j$ on the distal end side (the side close to the origin of the global coordinate system C) of the link $T_j$ is placed at the origin of the global coordinate system C. Additionally, the link $T_j$ is formed by linearly connecting the origin of the global coordinate system C with the coordinate $P'_1$ ($l_{xj}$, $l_{yj}$, $l_{zj}$). Moreover, when correcting a form of the link $T_j$ by the form correction sequentially implementing section 51 of the form correcting section 50, the form correction is carried out in the order starting from the link $T_j$ on the distal end side (the side close to the origin of the global coordinate system C). At this time, the sensor position compensating section 55 is configured to compensate a position of the sensor unit (the state compensation target sensor) $S_j$ on the proximal end side (the side far from the origin of the global coordinate system C) of the link (the correction target link) $T_j$ as a correction target. Therefore, the sensor position observing section 61 is configured to observe the sensor unit (the state compensation target sensor) $S_j$ on the proximal end side (the side far from the origin of the global coordinate system C) of the link (the correction target link) $T_j$ as a correction target for a predetermined number of times.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic form detection device comprising:
an endoscope including an inserting section in which sensor units are arranged in longitudinal directions at intervals of a predetermined inter-sensor dimension;
a posture detecting section configured to detect a posture of each of the sensor units based on measurement data in the sensor unit;
a linear form detecting section configured to detect a detected linear form of the inserting section of the endoscope on an assumption that a form between the respective sensor units is a linear link whose dimension is equal to the inter-sensor dimension based on the posture of each of the sensor units detected by the posture detecting section; and
a form correcting section configured to compensate at least a position of each of the sensor units by using a particle filter, and configured to detect a corrected form obtained by correcting the detected linear form detected by the linear form detecting section.

2. The device according to claim 1,
wherein the form correcting section includes:
a form correction sequentially implementing section configured to sequentially perform the form correction in accordance with each of the links in a global coordinate system having an origin at the center of the sensor unit on the most proximal end side or the most distal end side in the order from the link on a side close to the origin of the global coordinate system, and configured to form a corrected inter-sensor element which is a form between the respective sensor units in the corrected form; and
a form correction controlling section configured to control the form correction sequentially implementing section to perform the form correction with respect to all the links.

3. The device according to claim 2,
wherein the form correcting section includes an uncorrected link position compensating section configured to parallel translate a correction uncompleted portion constituted of an uncorrected link as the link which has not been subjected to the form correction in such a manner that a boundary between the correction uncompleted portion and a correction completed portion constituted of the corrected inter-sensor element formed by the form correction becomes continuous every time the form correction of one link is carried out by the form correction sequentially implementing section, and configured to compensate a position of the correction uncompleted portion.

4. The device according to claim 2,
wherein the form correction sequentially implementing section includes:
a sensor state estimating section configured to estimate at least a position of a state compensation target sensor, which is the sensor unit on a side far from the origin of the global coordinate system, in a correction target link, which is the link as a target of the form correction performed by the form correction sequentially implementing section, by using the particle filter based on an initial state of the state compensation target sensor before the form correction of the correction target link is effected by the form correction sequentially implementing section or an estimation result of the previous estimation; and
a state estimation controlling section configured to control the sensor state estimating section in such a manner that the estimation of the state compensation target sensor is performed for a predetermined number of times.

5. The device according to claim 4,
wherein the form correction sequentially implementing section includes:
a sensor state compensating section configured to compensate at least a position of the state compensation target sensor based on an estimation result in the sensor state estimating section; and
a corrected inter-sensor element forming section configured to form the corrected inter-sensor element based on a position of the state compensation target sensor compensated by the sensor state compensating section.

6. The device according to claim 4,
wherein the sensor state estimating section includes:
a particle dispersing section configured to disperse a predetermined number of particles based on the initial state of the state compensation target sensor or the estimation result of the previous estimation;
a particle moving section configured to detect a transfer model from a state of the inserting section of the endoscope and measurement data of each sensor unit, and configured to move each of the dispersed particles from a pre-movement particle position to a post-movement particle position based on the transfer model;
a weight calculating section configured to calculate likelihood representing how likely the state compensation target sensor is placed at the post-movement particle position of each particle, and configured to calculate a weight of each particle from the likelihood; and
a sensor state observing section configured to observe at least a position of the state compensation target sensor based on the weight of each particle calculated by the weight calculating section.

7. The device according to claim 6,
wherein the particle moving section is a curve interpolating section configured to detect the transfer model from a bent state of the inserting section of the endoscope, and configured to perform curve interpolation between the sensor unit on the side close to the origin of the global coordinate system of the correction target link and each particle based on the transfer model, the curve interpolating section being configured to move each particle.

8. The device according to claim 6,
wherein the particle moving section is a moving-state transfer model implementing section configured to detect the transfer model from an acceleration vector, a velocity vector, and displacement in the global coordinate system of each sensor unit detected in a moving state in which the inserting section of the endoscope is being parallel translated, and configured to move each particle based on the transfer model.

9. A form detecting method of an inserting section of an endoscope, the method comprising:
performing measurement by using sensor units arranged in longitudinal directions of the inserting section of the endoscope at intervals of a predetermined inter-sensor dimension;
detecting a posture of each sensor unit based on measurement data in each sensor unit by using a posture detecting section;
detecting a detected linear form of the inserting section of the endoscope by using a linear form detecting section on an assumption that a form between the respective sensor units is a linear link whose dimension is equal to the inter-sensor dimension based on the posture of each sensor unit detected by the posture detecting section; and
compensating at least a position of each sensor unit by using a particle filter, and detecting a corrected form obtained by correcting the detected linear form detected by the linear form detecting section by using a form correcting section.

10. The method according to claim 9,
wherein the compensating at least a position of each sensor unit and detecting the corrected form by the form correcting section includes:
sequentially performing form correction in accordance with each link in a global coordinate system having an origin at the center of the sensor unit on the most proximal end side or the most distal end side in the order starting from the link on a side close to the origin of the global coordinate system, and forming a corrected inter-sensor element which is a form between the respective sensor units in the corrected form by using a form correction sequentially implementing section of the form correcting section; and
controlling in such a manner that all the links are subjected to the form correction by the form correction sequentially implementing section by using a form correction controlling section of the form correcting section.

11. The method according to claim 10,
wherein the compensating at least a position of each sensor unit and detecting the corrected form by the form correcting section includes: parallel translating a correction uncompleted portion constituted of an uncorrected link, which is the link that has not been subjected to the form correction, in such a manner that a boundary between the correction uncompleted portion and a correction completed portion constituted of the corrected inter-sensor element formed by the form correction becomes continuous every time the form correction of one link is carried out by the form correction sequentially implementing section, and compensating a position of the correction uncompleted portion by using an uncorrected link position compensating section of the form correcting section.

12. The method according to claim 10, wherein the forming the corrected inter-sensor element by the form correction sequentially implementing section includes:

estimating at least a position of a state compensation target sensor, which is the sensor unit on the side far from the origin of the global coordinate system, in a correction target link, which is the link as a target of the form correction performed by the form correction sequentially implementing section, with the use of the particle filter based on an initial state of the state compensation target sensor before performing the form correction of the correction target link or an estimation result of the previous estimation by using a sensor state estimating section of the form correction sequentially implementing section; and controlling in such a manner that the estimation is carried out by the sensor state estimating section for a predetermined number of times by using a state estimation controlling section of the form correction sequentially implementing section.

13. The method according to claim 12, wherein the forming the corrected inter-sensor element by the form correction sequentially implementing section includes:

compensating at least a position of the state compensation target sensor by using a sensor state compensating section of the form correction sequentially implementing section based on an estimation result of the state compensation target sensor in the sensor state estimating section; and forming the corrected inter-sensor element by using a corrected inter-sensor element forming section of the form correction sequentially implementing section based on a position of the state compensation target sensor compensated by the sensor state compensating section.

14. The method according to claim 12, wherein the estimating at least a position of the state compensation target sensor by the sensor state estimating section includes:

dispersing a predetermined number of particles by using a particle dispersing section of the sensor state estimating section based on the initial state of the state compensation target sensor or the estimation result of the previous estimation;

detecting a transfer model from a state of the inserting section of the endoscope and measurement data in each sensor unit, and moving each of the particles dispersed by the particle dispersing section from a pre-movement particle position to a post-movement particle position by using a particle moving section of the sensor state estimating section;

calculating likelihood representing how likely the state compensating target sensor is placed at the post-movement particle position of each particle, and calculating a weight of each particle from the likelihood by using a weight calculating section of the sensor state estimating section; and observing at least a position of the state compensation target sensor based on the weight of each particle calculated by the weight calculating section by using a sensor state observing section of the sensor state estimating section.

15. The method according to claim 14, wherein the moving each particle by the particle moving section includes: detecting the transfer model from a bent state of the inserting section of the endoscope, performing curve interpolation between the sensor unit on the side close to the origin of the global coordinate system of the correction target link and each particle based on the transfer model, and moving each particle by using a curve interpolating section serving as the particle moving section.

16. The method according to claim 14, wherein the moving each particle by the particle moving section includes: detecting the transfer model from an acceleration vector, a velocity vector, and displacement in the global coordinate system of each sensor unit detected in a moving state in which the inserting section of the endoscope is being parallel translated, and moving each particle by using a moving-state transfer model implementing section serving as the particle moving section based on the transfer model.

* * * * *